(12) United States Patent
Nam et al.

(10) Patent No.: US 7,544,686 B2
(45) Date of Patent: Jun. 9, 2009

(54) PIPERAZINYLALKYLPYRAZOLE DERIVATIVES USEFUL AS SELECTIVE T-TYPE CALCIUM CHANNEL BLOCKERS AND PREPARATION METHOD THEREOF

(75) Inventors: Ghilsoo Nam, Seoul (KR); Kyung-Il Choi, Seoul (KR); Hun Yeong Koh, Seoul (KR); Ae Nim Pae, Seoul (KR); Hyewhon Rhim, Seoul (KR); In-Sung Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 114 days.

(21) Appl. No.: 11/509,769

(22) Filed: Aug. 25, 2006

(65) Prior Publication Data

US 2007/0049604 A1 Mar. 1, 2007

(30) Foreign Application Priority Data

Aug. 26, 2005 (KR) .................... 10-2005-0079095

(51) Int. Cl.
*A61K 31/415* (2006.01)
*A61K 31/4155* (2006.01)
*A61K 31/496* (2006.01)
*C07D 207/335* (2006.01)
*C07D 401/10* (2006.01)
*C07D 405/04* (2006.01)

(52) U.S. Cl. .................... 514/253.09; 514/254.05; 544/364; 544/371

(58) Field of Classification Search ............ None
See application file for complete search history.

(56) References Cited

U.S. PATENT DOCUMENTS 5,292,739 A 3/1994 Merce-Vidal et al.

FOREIGN PATENT DOCUMENTS

EP 0-497-659 A1 8/1992

WO WO-98/49149 A1 11/1998

OTHER PUBLICATIONS

Triggle, Biochemical Pharmacology vol. 74, p. 1-9 (2007).*
Pauwels, P.J. et al. (1999). "CA$^{++}$ and NA$^{++}$ Channels Involved in Neuronal Cell Death. Protection by Flunarizine," *Life Sciences.* 48:1881-1893.
Richard, S. et al. (1991). "Inhibition of T-type Calcium Currents by Dihydropyridines in Mouse Embryonic Dorsal Root Ganglion Neurons," *Neuroscience. Letters* 132(2):229-234.
Jung, H. K. et al. (2004). "Synthesis and Biological Evaluation of Novel T-type Ca$^{2+}$ Channel Blockers," *Bioorganic & Medicinal Chemistry* 12:3965-3970.
Lee, Y. S. et al. (2004). "3,4-Dihydroquinazoline Derivatives as Novel Selective T-type Ca$^{2+}$ Channel Blockers," *Bioorganic & Medicinal Chemistry Letters* 14:3379-3384.
Nam, G. et al. (2005). "Arylaminomethylpyrazole Derivatives as Ca$^{2+}$ Channel Blockers," *Scientific Abstract presented at The 13$^{th}$ International Conference of Women Engineers and Scientists in Seoul, Korea, Aug. 26-29, 2005.*

* cited by examiner

*Primary Examiner*—Emily Bernhardt
(74) *Attorney, Agent, or Firm*—Darby & Darby P.C.

(57) ABSTRACT

The present invention provides for novel piperazinylalkylpyrazole derivatives, the preparation method thereof and the selective T-type calcium channel blocking activity thereof. Particularly, it provides a piperazinylalkylpyrazole derivative as represented by the formula set forth below or its pharmaceutically acceptable salts, and its preparation method thereof.

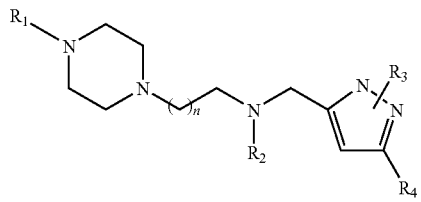

The compound of Formula 1 is a novel piperazinylalkylpyrazole derivative, which particulary has T-type Ca$^{2+}$ channel blocking effect and thus can be useful as a therapeutic agent for nerve and muscle pain.

9 Claims, No Drawings

PIPERAZINYLALKYLPYRAZOLE DERIVATIVES USEFUL AS SELECTIVE T-TYPE CALCIUM CHANNEL BLOCKERS AND PREPARATION METHOD THEREOF

BACKGROUND OF THE INVENTION

1. Field of the Invention

The present invention relates to piperazinylalkylpyrazole derivatives, the preparation method thereof and the selective T-type calcium channel blocking activity thereof.

2. Background of the Related Art

Depending on the response to membrane depolarization, calcium channels are classified into two main classes, high voltage activated (HVA) $Ca^{2+}$ channel and low voltage activated channel (LVA), and particularly, LVA $Ca^{2+}$ channel is also called as T-type $Ca^{2+}$ channel. $Ca^{2+}$ channels exist in neurons, heart, vascular smooth muscle and endocrine cells. The rise of concentration of $Ca^{2+}$ causes cell death or damage. Therefore, $Ca^{2+}$ channels are known to be involved in the contractions of atrium and smooth muscle, secretion of cortisol and dl-aldosterone in adrenal cortex, nerve stimulation and tissue development, etc. Inhibition of T-type $Ca^{2+}$ channel has been reported to have a treatment effect on neuropathic pain, high blood pressure and epilepsy.

Some well-known T-type $Ca^{2+}$ channel blockers are mibefradil (Ro 40-5967, WO 98/49149), flunarizine (Poauwels, P. J. et al. *J. Life. Sci.* 1991, 48, 18981), nicardipine (Richard, S. et al. *J. Neurosci. Lett.* 1991, 132 (2), 229) and a number of derivatives thereof. However, these drugs showed some undesirable side effects due to its pharmacokinetic interactions with other drugs metabolized by cytochromes P-450 3A4 and 2D6. Therefore, they are no longer in use. So it is very likely that the selective T-type channel blockers will be developed as an effective therapeutic agent for illnesses of neuropathic nerve and heart-related diseases, such as pain, epilepsy and high blood pressure.

T-type $Ca^{2+}$ channel antagonists such as piperazinylalkylisoxazole group (A. N. Pae et al. *Bioorganic. Med. Chem. Lett.* 2004, 12, 3965-3970) and 3,4-dihydroquinazoline derivatives have been recently reported. (Lee et al. *Bioorganic. Med. Chem. Lett.* 2004, 14, 3379-3384)

Therefore, an object of the present invention is to provide novel piperazinylalkylpyrazole derivatives or pharmaceutically acceptable salts thereof which have the possibility of being developed into a therapeutic agent for pain, high blood pressure, and epilepsy as a selective T-type $Ca^{2+}$ channel inhibitor, and the preparation methods thereof.

BRIEF DESCRIPTION OF THE INVENTION

An object of the present invention is to provide a piperazinylalkylpyrazole derivative or its pharmaceutically acceptable salt, and the preparation method thereof. Particularly, it is to provide the piperazinylalkylpyrazole derivative as represented by Formula 1 as set forth below or its pharmaceutically acceptable salt, and its preparation method thereof.

Formula 1

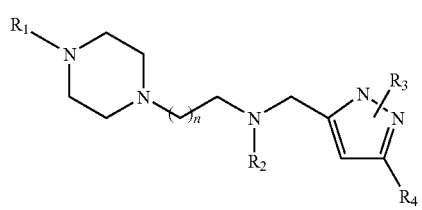

wherein, $R_1$ represents phenyl, X-substituted phenyl (X include nitro, methyl, chloro, methoxy, etc.; the substitution positions are ortho, meta, and para positions; and can be mono-, di-, tri-, tetra- or entirely-substituted), 1,1-diphenylmethyl, X-substituted diphenylmethyl (X represents chloro, methyl; the substitution position can be ortho, meta, and para positions; and mono, di, tri, tetra or all thereof can be substituted);

$R_2$ represents hydrogen, methyl or ethyl groups;

$R_3$ represents methyl, propyl, isobutyl, phenyl, cyclohexyl, substituted phenyl (wherein, the substituents are methyl, chloro, methoxy, etc.), naphthyl, piperidinyl groups;

$R_4$ represents hydrogen or $C_{1-6}$ lower alkyl, preferably methyl, ethyl, propyl, isopropyl, butyl, isobutyl, tertiary butyl, 2-furyl, phenyl, X-substituted phenyl(X represents chloro, methyl, cyclohexyl, piperidinyl, chloro groups, the substitution positions can be ortho, meta, and para positions and mono, di, tri, tetra or all thereof can be substituted); and n represents an integer from 0 to 3.

The compound of Formula 1 is a novel piperazinylalkylpyrazole derivative, which particularly has T-type $Ca^{2+}$ channel blocking effect and thus can be useful as a therapeutic agent for nerve and muscle pain. As the compound is believed have a treatment effect for epilepsy and high blood pressure, it is expected to replace the addictive pain killers such as morphine. The compound of Formula (I) ($R_2$=H), as represented in Reaction Scheme 1 below, can be produced by reaction between aldehyde compound as represented by Formula 3 and amine compound as represented by Formula 2 with presence of a suitable reducing agent.

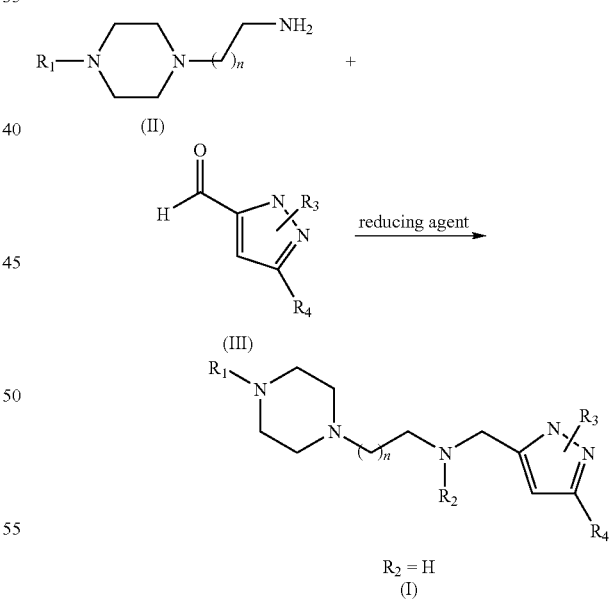

The reducing agents that can be used in the reaction represented by Reaction Scheme 1 are metal hydrides such as $NaBH_4$, $NaBH(OAc)_3$, $NaBH_2(OAc)_2$, $NaBH_3OAc$, $KBH_4$, $KBH(OAc)_3$, or $NaBH_3CN$, and it is preferable to use $NaBH(OAc)_3$.

As reaction solvents, various types of alcohol such as methanol, ethanol or propanol, tetrahydrofuran, chloroform, or alkyl halides such as methylene chloride can be used.

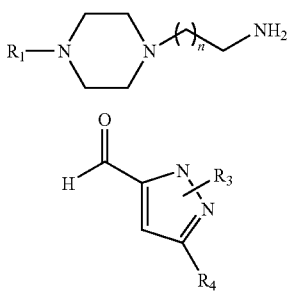

Formula 2

Formula 3

The amine represented in Formula 2 is 1-$R_1$ substituted-4-(2-aminoethyl)piperazine, and $R_1$ is the same as defined in Formula 1. These compounds were prepared from 1-$R_1$ substituted piperazine and N-1-bromoalkylimide, using a standard amine synthetic method called the Gabriel Synthesis (Gibson, M. S.; Bradshaw, R. W. *Angew. Chem. Int. Ed. Engl.* 1968, 7, 919).

The aldehyde as represented by Formula 3 was prepared by reducing the corresponding esters or oxidizing the corresponding alcohols. In Formula 3, $R_3$ and $R_4$ are defined the same as those in Formula 1.

In addition, the compound ($R_2$=methyl, ethyl) of Formula 1, as shown below in Reaction Scheme 2, can be prepared by using the aldehydes corresponding to the compound of Formula 1 ($R_2$=H) and reducing agents thereof, wherein NaBH(OAc)$_3$ is the most preferable metal hydride to be used as the reducing agent.

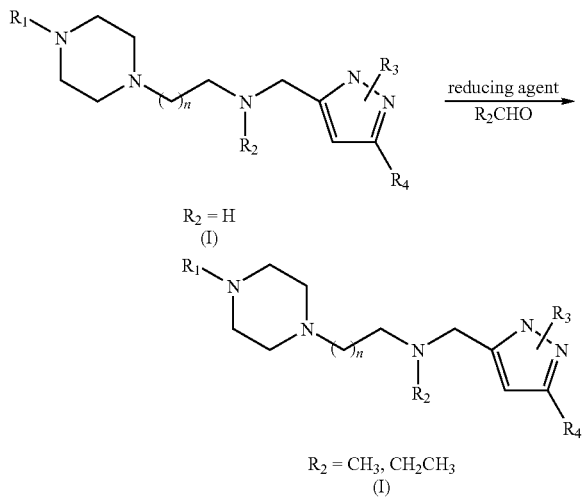

Reaction Scheme 2

DETAILED DESCRIPTION OF THE INVENTION

The preparation method and effects of the compound of the present invention is explained more in detail using the following examples. However, these examples only exemplifies the present invention, and therefore, the scope of the present invention is not limited to the following examples. In addition, the preparation methods of each corresponding piperazinylalkylamine and pyrazole-5-aldehyde are specifically described in the following References of the representative compounds.

Reference 1

Preparation of 2-[2-(4-phenylpiperazin-1-yl)ethyl]isoindole-1,3-dione 4-phenylpiperazine (4.50 g, 27.74 mmol) was dissolved in 30 ml DMF, then $K_2CO_3$ (11.50 g, 83.21 mmol) and N-(2-bromoethyl)phthalimide (8.46 g, 33.28 mmol) were added thereto and stirred at about 80° C. The reaction progress and completion were confirmed using TLC (hexane:EtOAc=1:1). Upon completion of the reaction, water was added to the reaction mixture and then was extracted with $CH_2Cl_2$. The organic layer was dried over anhydrous $MgSO_4$, filtered and concentrated under reduced pressure. The concentrate was separated by column chromatography (hexane:EtOAc:$CH_2Cl_2$=3:1:2) to obtain the titled compound.

Yield: 55.6%

$^1$H NMR (300 MHz, CDCl$_3$) δ 7.81 (m, 2H), 7.68 (m, 2H), 7.22 (m, 2H), 6.89 (d, J=7.41 Hz, 2H), 6.81 (t, J=7.23 Hz, 1H), 3.84 (t, J=6.84 Hz, 2H), 3.11 (t, J=4.71 Hz, 4H), 2.67 (m, 6H)

Reference 2

Preparation of 2-{2-[4-(2,3-dimethylphenyl)piperazin-1-yl]propyl}isoindole-1,3-dione Using the same method as in Reference 1, the above-mentioned compound was prepared by reacting 2-{2-[4-(2,3-dimethylphenyl)piperazine and N-(2-bromopropyl)phthalimide.

Yield: 93.7%

$^1$H NMR (300 MHz, CDCl$_3$) δ 7.86 (m, 2H), 7.72 (m, 2H), 7.06 (m, 1H), 6.88 (d, J=6.4 Hz, 1H), 6.76 (d, J=7.9 Hz, 1H), 3.81 (t, J=6.9 Hz, 2H), 2.73 (m, 4H), 2.51 (t, J=6.9 Hz, 4H), 2.29 (m, 2H), 2.25 (s, 3H), 2.18 (s, 3H), 1.92 (m, 2H)

Reference 3

Preparation of 2-[4-(2,3-dimethylphenyl)piperazin-1-yl]propylamine

2-{2-[4-(2,3-dimethylpropyl)piperazin-1-yl]propyl}isoindole-1,3-dione (3.0 g, 7.95 mmol) prepared in Reference 2 was dissolved in 50 ml EtOH, then $H_2NNH_2\cdot H_2O$ (1.54 ml, 31.80 mmol) was added and stirred at about 70° C. The reaction progress and completion were confirmed using TLC (hexane: EtOAc=1:1). Upon completion of the reaction, while the temperature was kept at room temperature, the resulting solution was filtered to remove insolubles. The solvent was removed by distilling it under reduced pressure, followed by adding water and extracting the aqueous layer with $CH_2Cl_2$. The organic layer was dried over anhydrous $MgSO_4$, filtered and concentrated under reduced pressure to obtain the title compound.

Yield: 44.7%

$^1$H NMR (300 MHz, CDCl$_3$) δ 7.05 (t, J=7.8 Hz, 1H), 6.91 (m, 2H), 3.61 (brs, 2H), 2.89 (m, 6H), 2.52 (m, 4H), 2.28 (m, 2H), 2.25 (s, 3H), 2.19 (s, 3H), 1.84 (m, 2H)

Reference 4

Preparation of 3-formyl-5-methylpyrazole

Under nitrogen environment, 3-ethoxycarbonyl-5-methylpyrazole (1.0 g, 4.34 mmol) was dissolved in 15 ml of purified toluene, and DIBAL (8.68 ml, 8.62 mmol) was slowly added and stirred at −78° C. The reaction progress and completion were confirmed using TLC (hexane:EtOAc=6:1). Upon completion of the reaction, MeOH and water were slowly added to the reaction mixture and the resulting mixture was filtered through a celite bed, and the aqueous layer was extracted with EtOAc. The organic layer was dried over anhydrous MgSO$_4$, filtered and concentrated under reduced pressure. The concentrate was separated by column chromatography (hexane:EtOAc:CH$_2$Cl$_2$=3:1:1) to obtain the title compound.

Yield: 82.4%

$^1$H NMR (300 MHz, CDCl$_3$) δ 9.92 (s, 1H), 6.68 (s, 1H), 2.82 (s, 3H)

Reference 5

Preparation of
1-tert-butyl-5-iso-butyl-3-formylpyrazole

PCC (0.67 g, 3.12 mmol) and silica gel (0.50 g) were grinded together and dispersed in 10 ml of purified CH$_2$Cl$_2$ followed by treatment with ultrasound at 20° C. for 30 minutes. 1-tert-butyl-5-iso-butyl-3-hydroxymethylpyrazole (0.50 g, 2.08 mmol) was dissolved in 10 ml of purified CH$_2$Cl$_2$ and the solution was added thereto and treated with ultrasound for 15 minutes. The reaction progress and completion were confirmed using TLC (hexane:EtOAc=6:1). Upon completion of the reaction, ether was added to the reaction mixture and then the resulting mixture was filtered through a celite bed, and concentrated under reduced pressure. The concentrate was separated by column chromatography (hexane:EtOAc:CH$_2$Cl$_2$=3:1:1) to obtain the compound of the present invention.

Yield: 88.8%

$^1$H NMR (300 MHz, CDCl$_3$) δ 9.86 (s, 1H), 6.79 (s, 1H), 2.51 (d, J=6.6 Hz, 2H), 1.94 (m, 1H), 1.68 (s, 9H), 0.95 (d, J=6.6 Hz, 6H)

EXAMPLE 1

Preparation of 5-methyl-3-[2-(4-phenylpiperazin-1-yl)ethyl]aminomethylpyrazole[Compound 1]

4-phenylpiperazin-1-ylethylamine (50 mg, 0.208 mmol) and 5-methylpyrazole-3-carbaldehyde (25.24 mg, 0.104 mmol) were dissolved in 5 ml of purified CH$_2$Cl$_2$, and then 4 Å Molecular sieve (5 beads) was added thereto and was stirred for 12 hours at room temperature. Then, NaBH(OAc)$_3$ (66.28 mg, 0.313 mmol) was added thereto and was stirred for 1 hour at room temperature. The reaction progress and completion were confirmed using TLC (CH$_2$Cl$_2$:MeOH=5:1). Upon completion of the reaction, water was added to the reaction mixture and the aqueous layer was extracted with CH$_2$Cl$_2$. The organic layer was dried over anhydrous MgSO$_4$, filtered and concentrated under reduced pressure. The concentrate was separated by column chromatography (CH$_2$Cl$_2$:MeOH=10:1) to obtain the titled compound.

Yield: 52.2%.

$^1$H NMR (300 MHz, CDCl$_3$) δ 7.27 (m, 2H), 6.82-6.95 (m, 3H), 6.17 (s, 1H), 4.56 (brs, 1H), 4.01 (s, 2H), 3.17 (t, J=4.8 Hz, 4H), 3.03 (t, J=5.8 Hz, 2H), 2.53-2.57 (m, 5H), 2.61 (t, J=4.8 Hz, 4H).

The compounds of the following examples were prepared using the same method as in Example 1 from the corresponding piperazinylamines and pyrazolealdehydes. The following Table 1 illustrates the corresponding piperazinylamines and pyrazolealdehydes used in Examples 2 to 106.

TABLE 1

| Example | piperazinylamine | pyrazole carbaldehyde |
| --- | --- | --- |
| 1 | 4-phenylpiperazin-1-ylethylamine | 5-methylpyrazole-3-carbaldehyde |
| 2 | same as above | 5-methyl-1-phenylpyrazole-3-carbaldehyde |
| 3 | same as above | 5-propyl-1-t-butylpyrazole-3-carbaldehyde |
| 4 | same as above | 5-propyl-1-phenylpyrazole-3-carbaldehyde |
| 5 | same as above | 1-t-butyl-5-iso-butylpyrazole-3-carbaldehyde |
| 6 | same as above | 2-t-butyl-5-iso-butylpyrazole-3-carbaldehyde |
| 7 | same as above | 5-iso-butyl-1-phenylpyrazole-3-carbaldehyde |
| 8 | same as above | 1-phenyl-5-(2-furyl)pyrazole-3-carbaldehyde |
| 9 | same as above | 1,5-diphenylpyrazole-3-carbaldehyde |
| 10 | same as above | 1-t-butyl-5-(4-methylphenyl)pyrazole-3-carbaldehyde |
| 11 | same as above | 5-(4-chlorophenyl)-1-t-butylpyrazole-3-carbaldehyde |
| 12 | same as above | 5-(4-cyclohexylphenyl)-1-phenylpyrazole-3-carbaldehyde |
| 13 | same as above | 1-phenyl-5-(4-(piperidin-1-yl)phenyl)pyrazole-3-carbaldehyde |
| 14 | 4-(2,3-dimethylphenyl)piperazin-1-ylethylamine | 5-methyl-1-phenylpyrazole-3-carbaldehyde |
| 15 | same as above | 5-propyl-1-t-butylpyrazole-3-carbaldehyde |
| 16 | same as above | 5-propyl-1-phenylpyrazole-3-carbaldehyde |
| 17 | same as above | 1-t-butyl-5-iso-butylpyrazole-3-carbaldehyde |
| 18 | same as above | 5-iso-butyl-1-phenylpyrazole-3-carbaldehyde |
| 19 | same as above | 1-phenyl-5-(2-furyl)pyrazole-3-carbaldehyde |
| 20 | same as above | 1,5-diphenylpyrazole-3-carbaldehyde |
| 21 | same as above | 1-t-butyl-5-(4-methylphenyl)pyrazole-3-carbaldehyde |
| 22 | same as above | 5-(4-chlorophenyl)-1-t-butylpyrazole-3-carbaldehyde |
| 23 | same as above | 5-(4-cyclohexylphenyl)-1-phenylpyrazole-3-carbaldehyde |
| 24 | same as above | 1-phenyl-5-(4-(piperidin-1-yl)phenyl)pyrazole-3-carbaldehyde |

TABLE 1-continued

| Example | piperazinylamine | pyrazole carbaldehyde |
|---|---|---|
| 25 | 4-(2,4-dimethylphenyl)piperazin-1-ylethylamine | 5-methyl-1-phenylpyrazole-3-carbaldehyde |
| 26 | same as above | 5-propyl-1-t-butylpyrazole-3-carbaldehyde |
| 27 | same as above | 5-propyl-1-phenylpyrazole-3-carbaldehyde |
| 28 | same as above | 1-t-butyl-5-iso-butylpyrazole-3-carbaldehyde |
| 29 | same as above | 5-iso-butyl-1-phenylpyrazole-3-carbaldehyde |
| 30 | same as above | 1-phenyl-5-(2-furyl)pyrazole-3-carbaldehyde |
| 31 | same as above | 1,5-diphenylpyrazole-3-carbaldehyde |
| 32 | same as above | 1-t-butyl-5-(4-methylphenyl)pyrazole-3-carbaldehyde |
| 33 | same as above | 5-(4-chlorophenyl)-1-t-butylpyrazole-3-carbaldehyde |
| 34 | same as above | 5-(4-cyclohexylphenyl)-1-phenylpyrazole-3-carbaldehyde |
| 35 | same as above | 1-phenyl-5-(4-(piperidin-1-yl)phenyl)pyrazole-3-carbaldehyde |
| 36 | 4-(4-methoxyphenyl)piperazin-1-ylethylamine | 5-methylpyrazole-3-carbaldehyde |
| 37 | same as above | 5-methyl-1-phenylpyrazole-3-carbaldehyde |
| 38 | same as above | 5-propyl-1-t-butylpyrazole-3-carbaldehyde |
| 39 | same as above | 5-propyl-1-phenylpyrazole-3-carbaldehyde |
| 40 | same as above | 1-t-butyl-5-iso-butylpyrazole-3-carbaldehyde |
| 41 | same as above | 2-t-butyl-5-iso-butylpyrazole-3-carbaldehyde |
| 42 | same as above | 5-iso-butyl-1-phenylpyrazole-3-carbaldehyde |
| 43 | same as above | 1-phenyl-5-(2-furyl)pyrazole-3-carbaldehyde |
| 44 | same as above | 1,5-diphenylpyrazole-3-carbaldehyde |
| 45 | same as above | 1-t-butyl-5-(4-methylphenyl)pyrazole-3-carbaldehyde |
| 46 | same as above | 5-(4-chlorophenyl)-1-t-butylpyrazole-3-carbaldehyde |
| 47 | same as above | 5-(4-cyclohexylphenyl)-1-phenylpyrazole-3-carbaldehyde |
| 48 | same as above | 1-phenyl-5-(4-(piperidin-1-yl)phenyl)pyrazole-3-carbaldehyde |
| 49 | 4-(4-nitrophenyl)piperazin-1-yl ethylamine | 5-methyl-1-phenylpyrazole-3-carbaldehyde |
| 50 | same as above | 5-propyl-1-t-butylpyrazole-3-carbaldehyde |
| 51 | same as above | 5-propyl-1-phenylpyrazole-3-carbaldehyde |
| 52 | same as above | 1-t-butyl-5-iso-butylpyrazole-3-carbaldehyde |
| 53 | same as above | 5-iso-butyl-1-phenylpyrazole-3-carbaldehyde |
| 54 | same as above | 1-phenyl-5-(2-furyl)pyrazole-3-carbaldehyde |
| 55 | same as above | 1,5-diphenylpyrazole-3-carbaldehyde |
| 56 | same as above | 1-t-butyl-5-(4-methylphenyl)pyrazole-3-carbaldehyde |
| 57 | same as above | 5-(4-chlorophenyl)-1-t-butylpyrazole-3-carbaldehyde |
| 58 | same as above | 5-(4-cyclohexylphenyl)-1-phenylpyrazole-3-carbaldehyde |
| 59 | same as above | 1-phenyl-5-(4-(piperidin-1-yl)phenyl)pyrazole-3-carbaldehyde |
| 60 | 4-(2-fluorophenyl)piperazin-1-ylethylamine | 5-methylpyrazole-3-carbaldehyde |
| 61 | same as above | 5-methyl-1-phenylpyrazole-3-carbaldehyde |
| 62 | same as above | 5-propyl-1-t-butylpyrazole-3-carbaldehyde |
| 63 | same as above | 5-propyl-1-phenylpyrazole-3-carbaldehyde |
| 64 | same as above | 1-t-butyl-5-iso-butylpyrazole-3-carbaldehyde |
| 65 | same as above | 2-t-butyl-5-iso-butylpyrazole-3-carbaldehyde |
| 66 | same as above | 5-iso-butyl-1-phenylpyrazole-3-carbaldehyde |
| 67 | same as above | 1-phenyl-5-(2-furyl)pyrazole-3-carbaldehyde |
| 68 | same as above | 1,5-diphenylpyrazole-3-carbaldehyde |
| 69 | same as above | 1-t-butyl-5-(4-methylphenyl)pyrazole-3-carbaldehyde |
| 70 | same as above | 5-(4-chlorophenyl)-1-t-butylpyrazole-3-carbaldehyde |
| 71 | same as above | 5-(4-cyclohexylphenyl)-1-phenylpyrazole-3-carbaldehyde |
| 72 | same as above | 1-phenyl-5-(4-(piperidin-1-yl)phenyl)pyrazole-3-carbaldehyde |
| 73 | 4-(3-chlorophenyl)piperazin-1-ylethylamine | 5-methylpyrazole-3-carbaldehyde |

TABLE 1-continued

| Example | piperazinylamine | pyrazole carbaldehyde |
|---|---|---|
| 74 | same as above | 5-methyl-1-phenylpyrazole-3-carbaldehyde |
| 75 | same as above | 5-propyl-1-t-butylpyrazole-3-carbaldehyde |
| 76 | same as above | 5-propyl-1-phenylpyrazole-3-carbaldehyde |
| 77 | same as above | 1-t-butyl-5-iso-butylpyrazole-3-carbaldehyde |
| 78 | same as above | 2-t-butyl-5-iso-butylpyrazole-3-carbaldehyde |
| 79 | same as above | 5-iso-butyl-1-phenylpyrazole-3-carbaldehyde |
| 80 | same as above | 1-phenyl-5-(2-furyl)pyrazole-3-carbaldehyde |
| 81 | 4-diphenylmethylpiperazin-1-ylethylamine | 5-methyl-1-phenylpyrazole-3-carbaldehyde |
| 82 | same as above | 5-propyl-1-t-butylpyrazole-3-carbaldehyde |
| 83 | same as above | 5-propyl-1-phenylpyrazole-3-carbaldehyde |
| 84 | same as above | 1-t-butyl-5-iso-butylpyrazole-3-carbaldehyde |
| 85 | same as above | 5-iso-butyl-1-phenylpyrazole-3-carbaldehyde |
| 86 | same as above | 1-phenyl-5-(2-furyl)pyrazole-3-carbaldehyde |
| 87 | same as above | 1,5-diphenylpyrazole-3-carbaldehyde |
| 88 | same as above | 1-t-butyl-5-(4-methylphenyl)pyrazole-3-carbaldehyde |
| 89 | same as above | 5-(4-chlorophenyl)-1-t-butylpyrazole-3-carbaldehyde |
| 90 | same as above | 5-(4-cyclohexylphenyl)-1-phenylpyrazole-3-carbaldehyde |
| 91 | same as above | 1-phenyl-5-(4-(piperidin-1-yl)phenyl)pyrazole-3-carbaldehyde |
| 92 | 4-(4-chlorobenzhydril)piperazin-1-ylethylamine | 5-methyl-1-phenylpyrazole-3-carbaldehyde |
| 93 | same as above | 5-propyl-1-t-butylpyrazole-3-carbaldehyde |
| 94 | same as above | 5-propyl-1-phenylpyrazole-3-carbaldehyde |
| 95 | same as above | 1-t-butyl-5-iso-butylpyrazole-3-carbaldehyde |
| 96 | same as above | 5-iso-butyl-1-phenylpyrazole-3-carbaldehyde |
| 97 | same as above | 1-phenyl-5-(2-furyl)pyrazole-3-carbaldehyde |
| 98 | same as above | 1,5-diphenylpyrazole-3-carbaldehyde |
| 99 | same as above | 1-t-butyl-5-(4-methylphenyl)pyrazole-3-carbaldehyde |
| 100 | same as above | 5-(4-chlorophenyl)-1-t-butylpyrazole-3-carbaldehyde |
| 101 | same as above | 5-(4-cyclohexylphenyl)-1-phenylpyrazole-3-carbaldehyde |
| 102 | same as above | 1-phenyl-5-(4-(piperidin-1-yl)phenyl)pyrazole-3-carbaldehyde |
| 103 | 4-(2,3-dimethylphenyl)piperazin-1-ylpropylamine | 5-methyl-1-phenylpyrazole-3-carbaldehyde |
| 104 | ? | 1,5-diphenylpyrazole-3-carbaldehyde |
| 105 | 4-diphenylmethylpiperazin-1-ylpropylamine | 5-methyl-1-phenylpyrazole-3-carbaldehyde |
| 106 | same as above | 1,5-diphenylpyrazole-3-carbaldehyde |

EXAMPLE 2

Synthesis of 5-methyl-1-phenyl-3-[2-(4-phenylpiperazin-1-yl)ethyl]aminomethylpyrazole [Compound 2]

Compound 2 was prepared using the same method as that of Example 1 except that 4-phenylpiperazin-1-ylethylamine and 5-methyl-1-phenylpyrazole-3-carbaldehyde were used.
Yield: 46.9%
$^1$H NMR (300 MHz, CDCl$_3$) δ 7.36-7.56 (m, 5H), 7.25 (m, 2H), 6.78-6.89 (m, 3H), 6.30 (s, 1H), 4.30 (brs, 1H), 4.10 (s, 2H), 2.91-3.23 (m, 12H), 2.74 (m, 3H)

EXAMPLE 3

Synthesis of 1-t-butyl-5-propyl-3-[2-(4-phenylpiperazin-1-yl)ethyl]aminomethylpyrazole [Compound 3]

Compound 3 was prepared using the same method as that of Example 1 except that 4-phenylpiperazin-1-ylethylamine and 5-propyl-1-t-butylpyrazole-3-carbaldehyde were used.

Yield: 64.2%
$^1$H NMR (300 MHz, CDCl$_3$) δ 7.27 (t, J=7.7 Hz, 2H), 6.93 (d, J=8.1 Hz, 2H), 6.86 (t, J=7.2 Hz, 1H), 6.04 (s, 1H), 3.98 (s, 2H), 3.20 (m, 4H), 2.84 (t, J=5.7 Hz, 2H), 2.58-2.70 (m, 6H), 2.54 (t, J=7.7 Hz, 2H), 1.56-1.77 (m, 11H), 0.96 (t, J=7.2 Hz, 3H)

EXAMPLE 4

Synthesis of 5-propyl-1-phenyl-3-[2-(4-phenylpiperazin-1-yl)ethyl]aminomethylpyrazole [Compound 4]

Compound 4 was prepared using the same method as that of Example 1 except that 4-phenylpiperazin-1-ylethylamine and 5-propyl-1-phenylpyrazole-3-carbaldehyde were used.
Yield: 55.6%
$^1$H NMR (300 MHz, CDCl$_3$) δ 7.33-7.52 (m, 6H), 7.26 (m, 2H), 6.88 (m, 2H), 6.35 (s, 1H), 3.91 (s, 2H), 3.20 (m, 4H), 2.87 (m, 2H), 2.71 (m, 4H), 2.54-2.67 (m, 4H), 1.62 (m, 2H), 0.93 (t, J=7.3 Hz, 3H)

EXAMPLE 5

Synthesis of 1-t-butyl-5-iso-butyl-3-[2-(4-phenylpiperazin-1-yl)ethyl]aminomethylpyrazole [Compound 5]

Compound 5 was prepared using the same method as that of Example 1 except that 4-phenylpiperazin-1-ylethylamine and 1-t-butyl-5-iso-butylpyrazole-3-carbaldehyde were used.

Yield: 25.8%

$^1$H NMR (300 MHz, CDCl$_3$) δ 7.27 (t, J=8.0 Hz, 2H), 6.93 (m, 2H), 6.86 (t, J=7.2 Hz, 1H), 6.00 (s, 1H), 3.95 (s, 2H), 3.19 (m, 4H), 2.81 (t, J=5.7 Hz, 2H), 2.54-2.69 (m, 6H), 2.42 (m, 2H), 1.88 (m, 1H), 1.62 (s, 9H), 0.92 (d, J=6.6 Hz, 6H)

EXAMPLE 6

Synthesis of 2-t-butyl-5-isobutyl-3-[2-(4-phenylpiperazin-1-yl)ethyl]aminomethylpyrazole [Compound 6]

Compound 6 was prepared using the same method as that of Example 1 except that 4-phenylpiperazin-1-ylethylamine and 2-t-butyl-5-iso-butylpyrazole-3-carbaldehyde were used.

Yield: 50.1%

$^1$H NMR (300 MHz, CDCl$_3$) δ 7.28 (t, J=7.6 Hz, 2H), 6.93 (m, 2H), 6.87 (t, J=7.1 Hz, 1H), 6.01 (s, 1H), 3.96 (s, 2H), 3.20 (m, 4H), 2.81 (t, J=5.6 Hz, 2H), 2.55-2.69 (m, 6H), 2.44 (d, J=7.1 Hz, 2H), 1.90 (m, 1H), 1.63 (s, 9H), 0.94 (d, J=6.5 Hz, 6H)

EXAMPLE 7

Synthesis of 5-iso-butyl-1-phenyl-3-[2-(4-phenylpiperazin-1-yl)ethyl]aminomethylpyrazole [Compound 7]

Compound 7 was prepared using the same method as used in Example 1 except that 4-phenylpiperazin-1-ylethylamine and 5-iso-butyl-1-phenylpyrazole-3-carbaldehyde were used.

Yield: 56.2%

$^1$H NMR (300 MHz, CDCl$_3$) δ 7.24-7.44 (m, 5H), 7.16 (m, 2H), 6.79 (m, 3H), 6.10 (s, 1H), 3.81 (s, 2H), 3.09 (m, 4H), 2.77 (t, J=5.6 Hz, 2H), 2.46-2.64 (m, 6H), 2.43 (d, J=7.0 Hz, 2H), 1.75 (m, 1H), 0.79 (d, J=6.3 Hz, 6H)

EXAMPLE 8

Synthesis of 5-(furan-2-yl)-1-phenyl-3-[2-(4-phenylpiperazin-1-yl)ethyl]aminomethylpyrazole [Compound 8]

Compound 8 was prepared using the same method as that of Example 1 except that 4-phenylpiperazin-1-ylethylamine and 1-phenyl-5-(2-furyl)pyrazole-3-carbaldehyde were used.

Yield: 69.2%

$^1$H NMR (300 MHz, CDCl$_3$) δ 7.34-7.59 (m, 6H), 7.23 (m, 2H), 6.78-6.97 (m, 3H), 6.75 (m, 1H), 6.32 (s, 1H), 6.98 (s, 1H), 3.96 (s, 2H), 3.27 (m, 4H), 3.06 (m, 2H), 2.91 (m, 4H), 2.82 (m, 2H)

EXAMPLE 9

Synthesis of 1,5-diphenyl-3-[2-(4-phenylpiperazin-1-yl)ethyl]aminomethylpyrazole [Compound 9]

Compound 9 was prepared using the same method as that of Example 1 except that 4-phenylpiperazin-1-ylethylamine and 1,5-diphenylpyrazole-3-carbaldehyde were used.

Yield: 78.8%

$^1$H NMR (300 MHz, CDCl$_3$) δ 7.28-7.38 (m, 9H), 7.18-7.26 (m, 3H), 6.81-6.91 (m, 3H), 6.60 (s, 1H), 4.23 (brs, 1H), 4.08 (s, 2H), 3.15 (t, J=4.6 Hz, 4H), 3.01 (t, J=5.9 Hz, 2H), 2.70 (t, J=5.9 Hz, 2H), 2.63 (t, J=4.6 Hz, 4H)

EXAMPLE 10

Synthesis of 1-t-butyl-5-(4-methylphenyl)-3-[2-(4-phenylpiperazin-1-yl)ethyl]aminomethylpyrazole [Compound 10]

Compound 10 was prepared using the same method as that of Example 1 except that 4-phenylpiperazin-1-ylethylamine and 1-t-butyl-5-(4-methylphenyl)pyrazole-3-carbaldehyde were used.

Yield: 80.0%

$^1$H NMR (300 MHz, CDCl$_3$) δ 7.13-7.33 (m, 6H), 6.87 (m, 3H), 6.30 and 6.15 (s, 1H), 4.98 (brs, 1H), 4.24 and 3.95 (s, 2H), 3.27 (m, 2H), 3.17 (m, 4H), 2.91 (m, 4H), 2.66 (m, 2H), 2.39 (s, 3H), 1.41 (s, 9H)

EXAMPLE 11

Synthesis of 1-t-butyl-5-(4-chlorophenyl)-3-[2-(4-phenylpiperazin-1-yl)ethyl]aminomethylpyrazole [Compound 11]

Compound 11 was prepared using the same method as that of Example 1 except that 4-phenylpiperazin-1-ylethylamine and 5-(4-chlorophenyl)-1-t-butylpyrazole-3-carbaldehyde were used.

Yield: 69.1%

$^1$H NMR (300 MHz, CDCl$_3$) δ 7.15-7.47 (m, 6H), 6.85 (m, 3H), 6.40 and 6.17 (s, 1H), 4.90 (brs, 1H), 4.24 and 3.99 (s, 2H), 2.51-3.38 (m, 12H), 1.41 (s, 9H)

EXAMPLE 12

Synthesis of 5-(4-cyclohexylphenyl)-1-phenyl-3-[2-(4-phenylpiperazin-1-yl)ethyl]aminomethylpyrazole [Compound 12]

Compound 12 was prepared using the same method as that of Example 1 except that 4-phenylpiperazin-1-ylethylamine and 5-(4-cyclohexylphenyl)-1-phenylpyrazole-3-carbaldehyde were used.

Yield: 71.2%

$^1$H NMR (300 MHz, CDCl$_3$) δ 7.19-7.40 (m, 7H), 7.06-7.19 (m, 4H), 6.81-7.13 (m, 3H), 6.63 and 6.52 (s, 1H), 4.60 (brs, 1H), 4.17 and 3.91 (s, 2H), 3.04-3.24 (m, 6H), 2.54-2.87 (m, 6H), 2.48 (m, 1H), 1.78 (m, 4H), 1.14-1.49 (m, 6H)

EXAMPLE 13

Synthesis of 1-phenyl-3-[2-(4-phenylpiperazin-1-yl)ethyl]aminomethyl-5-(4-piperidin-1-yl)phenylpyrazole [Compound 13]

Compound 13 was prepared using the same method as that of Example 1 except that 4-phenylpiperazin-1-ylethylamine and 1-phenyl-5-(4-(piperidine-1-yl)phenyl)pyrazole-3-carbaldehyde were used.

Yield: 58.4%

$^1$H NMR (300 MHz, CDCl$_3$) δ 7.16-7.39 (m, 7H), 7.07 (t, J=7.3 Hz, 2H), 6.74-6.91 (m, 5H), 6.53 and 6.42 (s, 1H), 3.69 and 3.57 (s, 2H), 3.04-3.33 (m, 10H), 2.85 (m, 4H), 2.65 (m, 2H), 1.68 (m, 4H), 1.60 (m, 2H)

EXAMPLE 14

Synthesis of 3-{2-[4-(2,3-dimethylphenyl)piperazin-1-yl]ethyl}aminomethyl-5-methyl-1-phenylpyrazole [Compound 14]

Compound 14 was prepared using the same method as that of Example 1 except that 4-(2,3-dimethylphenyl)piperazin-1-ylethylamine and 5-methyl-1-phenylpyrazole-3-carbaldehyde were used.

Yield: 85.6%

$^1$H NMR (300 MHz, CDCl$_3$) δ 7.32-7.53 (m, 5H), 7.06 (t, J=7.6 Hz, 1H), 6.90 (d, J=7.2 Hz, 1H), 6.84 (d, J=7.9 Hz, 1H), 6.35 and 6.32 (s, 1H), 4.06 (s, 1H), 3.00 (t, J=5.9 Hz, 2H), 2.89-2.95 (m, 6H), 2.73 (t, J=6.0 Hz, 4H), 2.64 (m, 3H), 2.41 (s, 3H), 2.20 (s, 3H)

EXAMPLE 15

Synthesis of 1-t-butyl-3-{2-[4-(2,3-dimethyl phenyl)piperazin-1-yl]ethyl}aminomethyl-5-propylpyrazole [Compound 15]

Compound 15 was prepared using the same method as that of Example 1 except that 4-(2,3-dimethylphenyl)piperazin-1-ylethylamine and 5-propyl-1-t-butylpyrazole-3-carbaldehyde were used.

Yield: 90.7%

$^1$H NMR (300 MHz, CDCl$_3$) δ 7.10 (t, J=7.7 Hz, 1H), 6.93 (m, 2H), 6.07 (s, 1H), 3.97 (s, 1H), 2.91 (m, 4H), 2.84 (t, J=5.8 Hz, 2H), 2.58-2.71 (m, 6H), 2.56 (t, J=7.8 Hz, 2H), 2.29 (s, 3H), 2.24 (s, 3H), 1.56-1.72 (m, 11H), 0.99 (t, J=7.3 Hz, 3H)

EXAMPLE 16

Synthesis of 3-{2-[4-(2,3-dimethylphenyl)piperazin-1-yl]ethyl}aminomethyl-1-phenyl-5-propylpyrazole [Compound 16]

Compound 16 was prepared using the same method as that of Example 1 except that 4-(2,3-dimethylphenyl)piperazin-1-ylethylamine and 5-propyl-1-phenylpyrazole-3-carbaldehyde were used.

Yield: 69.2%

$^1$H NMR (300 MHz, CDCl$_3$) δ 7.32-7.54 (m, 5H), 7.05 (t, J=7.6 Hz, 1H), 6.89 (d, J=7.2 Hz, 1H), 6.81 (d, J=7.9 Hz, 1H), 6.36 (s, 1H), 4.46 (brs, 1H), 4.08 (s, 2H), 3.02 (t, J=5.9 Hz, 2H), 2.83 (m, 4H), 2.74 (t, J=5.9 Hz, 4H), 2.48-2.69 (m, 6H), 2.26 (s, 3H), 2.22 (s, 3H), 1.62 (m, 2H), 0.92 (t, J=7.3 Hz, 3H)

EXAMPLE 17

Synthesis of 1-t-butyl-5-iso-butyl-3-{2-[4-(2,3-dimethylphenyl)piperazin-1-yl]ethyl}aminomethylpyrazole [Compound 17]

Compound 17 was prepared using the same method as that of Example 1 except that 4-(2,3-dimethylphenyl)piperazin-1-ylethylamine and 1-t-butyl-5-iso-butylpyrazole-3-carbaldehyde were used.

Yield: 90.8%

$^1$H NMR (300 MHz, CDCl$_3$) δ 7.10 (t, J=7.7 Hz, 1H), 6.92 (m, 2H), 6.03 (s, 1H), 3.97 (s, 2H), 2.92 (t, J=4.6 Hz, 4H), 2.83 (t, J=5.9 Hz, 2H), 2.56-2.72 (m, 6H), 2.45 (d, J=7.1 Hz, 2H), 2.29 (s, 3H), 2.24 (s, 3H), 1.89 (m, 1H), 1.65 (s, 9H), 0.95 (d, J=6.6 Hz, 6H)

EXAMPLE 18

Synthesis of 5-iso-butyl-3-{2-[4-(2,3-dimethyl phenyl)piperazin-1-yl]ethyl}aminomethyl-1-phenylpyrazole [Compound 18]

Compound 18 was prepared using the same method as that of Example 1 except that 4-(2,3-dimethylphenyl)piperazin-1-ylethylamine and 5-iso-butyl-1-phenylpyrazole-3-carbaldehyde were used.

Yield: 96.5%

$^1$H NMR (300 MHz, CDCl$_3$) δ 7.33-7.52 (m, 5H), 7.06 (t, J=7.7 Hz, 1H), 6.90 (d, J=7.3 Hz, 1H), 6.85 (d, J=7.9 Hz, 1H), 6.28 (s, 1H), 4.01 (s, 2H), 2.95 (t, J=6.0 Hz, 2H), 2.86 (t, J=4.5 Hz, 4H), 2.69 (t, J=6.0 Hz, 2H), 2.62 (m, 4H), 2.51 (d, J=7.1 Hz, 2H), 2.27 (s, 3H), 2.22 (s, 3H), 1.83 (m, 1H), 0.87 (d, J=6.6 Hz, 6H)

EXAMPLE 19

Synthesis of 3-{2-[4-(2,3-dimethylphenyl)piperazin-1-yl]ethyl}aminomethyl-5-(furan-2-yl)-1-phenylpyrazole [Compound 19]

Compound 19 was prepared using the same method as that of Example 1 except that 4-(2,3-dimethylphenyl)piperazin-1-ylethylamine and 1-phenyl-5-(2-furyl)pyrazole-3-carbaldehyde were used.

Yield: 77.9%

$^1$H NMR (300 MHz, CDCl$_3$) δ 7.36-7.52 (m, 6H), 7.07 (t, J=7.7 Hz, 1H), 6.88 (m, 2H), 6.72 and 6.65 (s, 1H), 6.33 (m, 1H), 5.97 (d, J=3.2 Hz, 1H), 3.94 and 3.82 (s, 2H) 3.38 (brs, 1H), 2.95 (t, J=6.1 Hz, 2H), 2.87 (t, J=4.3 Hz, 4H), 2.53-2.75 (m, 6H), 2.27 (s, 3H), 2.21 (s, 3H)

EXAMPLE 20

Synthesis of 3-{2-[4-(2,3-dimethyl phenyl)piperazin-1-yl]ethyl}aminomethyl-1,5-diphenylpyrazole [Compound 20]

Compound 20 was prepared using the same method as that of Example 1 except that 4-(2,3-dimethylphenyl)piperazin-1-ylethylamine and 1,5-diphenylpyrazole-3-carbaldehyde were used.

Yield: 72.9%

$^1$H NMR (300 MHz, CDCl$_3$) δ 7.19-7.37 (m, 10H), 7.05 (t, J=7.7 Hz, 1H), 6.90 (d, J=7.3 Hz, 1H), 6.80 (d, J=7.9 Hz, 1H), 6.68 (s, 1H), 4.16 (s, 3H), 3.08 (t, J=5.9 Hz, 2H), 2.85 (t, J=4.3 Hz, 4H), 2.77 (t, J=5.9 Hz, 2H), 2.66 (m, 4H)

EXAMPLE 21

Synthesis of 1-t-butyl-3-{2-[4-(2,3-dimethyl phenyl)piperazin-1-yl]ethyl}aminomethyl-5-(4-methyl)phenylpyrazole [Compound 21]

Compound 21 was prepared using the same method as that of Example 1 except that 4-(2,3-dimethylphenyl)piperazin-1-ylethylamine and 1-t-butyl-5-(4-methylphenyl)pyrazole-3-carbaldehyde were used.

Yield: 71.1%

$^1$H NMR (300 MHz, CDCl$_3$) δ 7.14-7.25 (m, 5H), 7.07 (t, J=7.8 Hz, 1H), 6.90 (m, 2H), 6.18 and 6.06 (s, 1H), 4.59 (brs, 1H), 4.06 and 3.76 (s, 2H), 3.07 (t, J=5.8 Hz, 2H), 2.89 (m, 4H), 2.77 (t, J=5.8 Hz, 2H), 2.66 (m, 4H), 2.41 (s, 3H), 2.27 (s, 3H), 2.22 (s, 3H), 1.44 (s, 9H)

EXAMPLE 22

Synthesis of 1-t-butyl-3-{2-[4-(2,3-dimethyl phenyl)piperazin-1-yl]ethyl}aminomethyl-5-(4-chlorophenyl)pyrazole [Compound 22]

Compound 22 was prepared using the same method as that of Example 1 except that 4-(2,3-dimethylphenyl)piperazin-1-ylethylamine and 5-(4-chlorophenyl)-1-t-butylpyrazole-3-carbaldehyde were used.

Yield: 77.8%

$^1$H NMR (300 MHz, CDCl$_3$) δ 7.35 (m, 2H), 7.27 (m, 2H), 7.08 (t, J=7.7 Hz, 1H), 6.89 (m, 2H), 6.36 (brs, 1H), 6.23 (s, 1H), 4.12 (s, 2H), 3.11 (m, 2H), 2.89 (m, 4H), 2.81 (m, 2H), 2.67 (m, 4H), 2.27(s, 3H), 2.21 (s, 3H), 1.43 (s, 9H)

EXAMPLE 23

Synthesis of 5-(4-cyclohexyl)phenyl-3-{2-[4-(2,3-dimethyl phenyl)piperazin-1-yl]ethyl}aminomethyl-1-phenylpyrazole [Compound 23]

Compound 23 was prepared using the same method as that of Example 1 except that 4-(2,3-dimethylphenyl)piperazin-1-ylethylamine and 5-(4-cyclohexyl phenyl)-1-phenylpyrazole-3-carbaldehyde were used.

Yield: 92.1%

$^1$H NMR (300 MHz, CDCl$_3$) δ 7.26-7.38 (m, 5H), 7.02-7.17 (m, 4H), 6.91 (m, 2H), 6.83 (d, J=7.9 Hz, 1H), 6.55 and 6.34 (s, 1H), 5.04 (brs, 2H), 4.07 and 3.97 (s, 2H), 2.94 (t, J=4.6 Hz, 2H), 2.85 (t, J=4.3 Hz, 2H), 2.55-2.82 (m, 8H), 2.49 (m, 1H), 2.27 (m, 3H), 2.20 (m, 3H), 1.68-1.95 (m, 6H), 1.40 (m, 4H)

EXAMPLE 24

Synthesis of 3-{2-[4-(2,3-dimethylphenyl)piperazin-1-yl]ethyl}aminomethyl-1-phenyl-5-(4-piperidin-1-yl)phenylpyrazole [Compound 24]

Compound 24 was prepared using the same method as that of Example 1 except that 4-(2,3-dimethylphenyl)piperazin-1-ylethylamine and 1-phenyl-5-(4-(piperidin-1-yl)phenyl)pyrazole-3-carbaldehyde were used.

Yield: 65.2%

$^1$H NMR (300 MHz, CDCl$_3$) δ 7.29-7.38 (m, 5H), 7.01-7.13 (m, 4H), 6.91 (t, J=8.1 Hz, 1H), 6.81 (m, 2H), 6.51 (s, 1H), 4.08 (s, 2H), 3.19 (t, J=5.2 Hz, 4H), 3.03 (t, J=5.9 Hz, 2H), 2.83 (m, 4H), 2.73 (t, J=5.9 Hz, 2H), 2.64 (m, 4H), 2.26 (s, 3H), 2.19 (s, 3H), 1.65-1.77 (m, 6H)

EXAMPLE 25

Synthesis of 3-{2-[4-(2,4-dimethyl phenyl)piperazin-1-yl]ethyl}aminomethyl-5-methyl-1-phenylpyrazole [Compound 25]

Compound 25 was prepared using the same method as that of Example 1 except that 4-(2,4-dimethylphenyl)piperazin-1-ylethylamine and 5-methyl-1-phenylpyrazole-3-carbaldehyde were used.

Yield: 39.3%

$^1$H NMR (300 MHz, CDCl$_3$) δ 7.32-7.58 (m, 5H), 6.91-7.04 (m, 3H), 6.21 (s, 1H), 3.85 (s, 2H), 2.89 (m, 4H), 2.74 (t, J=5.6 Hz, 2H), 2.48-2.66 (m, 6H), 2.34 (s, 3H), 2.27 (s, 6H)

EXAMPLE 26

Synthesis of 1-t-butyl-3-{2-[4-(2,4-dimethylphenyl)piperazin-1-yl]ethyl}aminomethyl-5-propylpyrazole [Compound 26]

Compound 26 was obtained using the same method as that of Example 1 except that 4-(2,4-dimethylphenyl)piperazin-1-ylethylamine and 5-propyl-1-t-butylpyrazole-3-carbaldehyde were used.

Yield: 79.4%

$^1$H NMR (300 MHz, CDCl$_3$) δ 6.89-7.05 (m, 3H), 6.06 (s, 1H), 3.97 (s, 2H), 2.91 (t, J=4.2 Hz, 4H), 2.83 (t, J=5.9 Hz, 2H), 2.48-2.67 (m, 6H), 2.28 (s, 6H), 1.64 (s, 9H), 0.98 (t, J=7.3 Hz, 3H)

EXAMPLE 27

Synthesis of 3-{2-[4-(2,4-dimethylphenyl)piperazin-1-yl]ethyl}aminomethyl-1-phenyl-5-propylpyrazole [Compound 27]

Compound 27 was prepared using the same method as that of Example 1 except that 4-(2,4-dimethylphenyl)piperazin-1-ylethylamine and 5-propyl-1-phenylpyrazole-3-carbaldehyde were used.

Yield: 73.6%

$^1$H NMR (300 MHz, CDCl$_3$) δ 7.33-7.52 (m, 5H), 6.82-7.02 (m, 3H), 6.40 and 6.29 (s, 1H), 4.27 (brs, 1H), 4.18 and 3.89 (s, 2H), 2.64-3.15 (m, 12H), 2.59 (m, 2H), 2.26 (s, 3H), 2.22 (s, 3H), 1.61 (m, 1H), 0.91 (m, 3H)

EXAMPLE 28

Synthesis of 1-t-butyl-5-iso-butyl-3-{2-[4-(2,4-dimethylphenyl)piperazin-1-yl]ethyl}aminomethylpyrazole [Compound 28]

Compound 28 was prepared using the same method as that of Example 1 except that 4-(2,4-dimethylphenyl)piperazin-1-ylethylamine and 1-t-butyl-5-iso-butylpyrazole-3-carbaldehyde were used.

Yield: 98.7%

$^1$H NMR (300 MHz, CDCl$_3$) δ 6.91-7.04 (m, 3H), 6.03 (s, 1H), 3.97 (s, 2H), 2.91 (m, 4H), 2.83 (t, J=5.8 Hz, 2H), 2.55-2.71 (m, 6H), 2.45 (d, J=7.1 Hz, 2H), 2.29 (s, 6H), 1.91 (m, 1H), 1.64 (s, 9H), 0.94 (d, J=9.5 Hz, 6H)

EXAMPLE 29

Synthesis of 5-iso-butyl-3-{2-[4-(2,4-dimethyl phenyl)piperazin-1-yl]ethyl}aminomethyl-1-phenylpyrazole [Compound 29]

Compound 29 was prepared using the same method as that of Example 1 except that 4-(2,4-dimethylphenyl)piperazin-1-ylethylamine and 5-iso-butyl-1-phenylpyrazole-3-carbaldehyde were used.

Yield: 69.2%

$^1$H NMR (300 MHz, CDCl$_3$) δ 7.31-7.52 (m, 5H), 6.86-7.02 (m, 3H), 6.39 and 6.27 (s, 1H), 4.39 (brs, 1H), 4.19 and 3.90 (s, 2H), 3.09 (m, 2H), 2.66-3.02 (m, 8H), 2.62 (m, 2H), 2.50 (m, 2H), 2.26 (s, 3H), 2.21 (s, 3H), 1.80 (m, 1H), 0.85 (m, 6H)

EXAMPLE 30

Synthesis of 3-{2-[4-(2,4-dimethylphenyl)piperazin-1-yl]ethyl}aminomethyl-5-(furan-2-yl)-1-phenylpyrazole [Compound 30]

Compound 30 was prepared using the same method as that of Example 1 except that 4-(2,4-dimethylphenyl)piperazin-1-ylethylamine and 1-phenyl-5-(2-furyl)pyrazole-3-carbaldehyde were used.

Yield: 92.2%

$^1$H NMR (300 MHz, CDCl$_3$) δ 7.28-7.51 (m, 6H), 6.90 (m, 3H), 6.76 (s, 1H), 6.30 (m, 1H), 5.97 (d, J=2.9 Hz, 1H), 4.99 (brs, 1H), 3.93 (s, 2H), 2.55-3.42 (m, 12H), 2.25 (s, 3H), 2.18 (s, 3H)

EXAMPLE 31

Synthesis of 3-{2-[4-(2,4-dimethyl phenyl)piperazin-1-yl]ethyl}aminomethyl-1,5-diphenylpyrazole [Compound 31]

Compound 31 was prepared using the same method as that of Example 1 except that 4-(2,4-dimethylphenyl)piperazin-1-ylethylamine and 1,5-diphenylpyrazole-3-carbaldehyde were used.

Yield: 89.1%

$^1$H NMR (300 MHz, CDCl$_3$) δ 7.27-7.38 (m, 8H), 7.23 (m, 2H), 6.97 (t, J=8.3 Hz, 2H), 6.86 (d, J=8.0 Hz, 1H), 6.60 (s, 1H), 4.30 (brs, 1H), 4.07 (s, 2H), 3.00 (t, J=5.9 Hz, 2H), 2.87 (m, 4H), 2.71 (t, J=5.9 Hz, 2H), 2.64 9m, 4H), 2.28 (s, 3H), 2.26 (s, 3H)

EXAMPLE 32

Synthesis of 1-t-butyl-3-{2-[4-(2,4-dimethyl phenyl)piperazin-1-yl]ethyl}aminomethyl-5-(4-methyl)phenylpyrazole [Compound 32]

Compound 32 was prepared using the same method as that of Example 1 except that 4-(2,4-dimethylphenyl)piperazin-1-ylethylamine and 1-t-butyl-5-(4-methylphenyl)pyrazole-3-carbaldehyde were used.

Yield: 67.0%

$^1$H NMR (300 MHz, CDCl$_3$) δ 7.12-7.24 (m, 4H), 6.86-7.03 (m, 3H), 6.25 and 6.10 (s, 1H), 4.75 (brs, 1H), 4.15 and 3.86 (s, 2H), 3.13 (t, J=5.8 Hz, 2H), 2.89 (m, 4H), 2.82 (t, J=5.8 Hz, 2H), 2.65 (m, 4H), 2.42 (s, 3H), 2.27 (s, 3H), 2.25 (s, 3H), 1.43 (s, 9H)

EXAMPLE 33

Synthesis of 1-t-butyl-5-(4-chlorophenyl)-3-{2-[4-(2,4-dimethylphenyl)piperazin-1-yl]-ethyl}aminomethylpyrazole [Compound 33]

Compound 33 was prepared using the same method as that of Example 1 except that 4-(2,4-dimethylphenyl)piperazin-1-ylethylamine and 5-(4-chlorophenyl)-1-t-butyl pyrazole-3-carbaldehyde were used.

Yield: 60.3%

$^1$H NMR (300 MHz, CDCl$_3$) δ 7.19-7.43 (m, 4H), 6.85-7.05 (m, 3H), 6.30 and 6.12 (s, 1H), 5.42 (brs, 1H), 4.13 and 3.84 (s, 2H), 2.54-3.18 (m, 12H), 2.26 (m, 6H), 1.42 (s, 9H)

EXAMPLE 34

Synthesis of 5-(4-cyclohexyl phenyl)-3-{2-[4-(2,4-dimethylphenyl)piperazin-1-yl]ethyl}aminomethyl-1-phenylpyrazole [Compound 34]

Compound 34 was prepared using the same method as that of Example 1 except that 4-(2,4-dimethylphenyl)piperazin-1-ylethylamine and 5-(4-cyclohexyl phenyl)-1-phenyl pyrazole-3-carbaldehyde were used.

Yield: 52.8%

$^1$H NMR (300 MHz, CDCl$_3$) δ 7.19-7.37 (m, 5H), 7.03-7.17 (m, 4H), 6.84-7.01 (m, 3H), 6.61 (s, 1H), 5.4 (brs, 1H), 3.93 (s, 2H), 2.68-3.26 (m, 12H), 2.46 (m, 1H), 2.21 (m, 6H), 1.66-1.95 (m, 6H), 1.37 (m, 4H)

EXAMPLE 35

Synthesis of 3-{2-[4-(2,4-dimethylphenyl)piperazin-1-yl]ethyl}aminomethyl-1-phenyl-5-(4-piperidin-1-yl)phenylpyrazole [Compound 35]

Compound 35 was prepared using the same method as that of Example 1 except that 4-(2,4-dimethylphenyl)piperazin-1-ylethylamine and 1-phenyl-5-(4-(piperidin-1-yl)phenyl)pyrazole-3-carbaldehyde were used.

Yield: 56.2%

$^1$H NMR (300 MHz, CDCl$_3$) δ 7.24-7.38 (m, 3H), 7.02-7.13 (m, 3H), 6.87-7.01 (m, 3H), 6.74-6.86 (m, 3H), 6.55 and 6.47 (s, 1H), 4.63 (brs, 1H), 4.13 and 3.91 (s, 2H), 3.18 (m, 4H), 3.05 (m, 2H), 2.83 (m, 4H), 2.76 (m, 2H), 2.63 (m, 4H), 2.27 (s, 3H), 2.24 (s, 3H), 1.54-1.75 (m, 6H)

EXAMPLE 36

Synthesis of 3-{2-[4-(4-methoxyphenyl)piperazin-1-yl]ethyl}aminomethyl-5-methylpyrazole [Compound 36]

Compound 36 was prepared using the same method as that of Example 1 except that 4-(4-methoxyphenyl)piperazin-1-ylethylamine and 5-methylpyrazole-3-carbaldehyde were used.

Yield: 30.1%

$^1$H NMR (300 MHz, CDCl$_3$) δ 6.76-6.97 (m, 4H), 6.17 (s, 1H), 4.86 (brs, 1H), 3.97 (s, 2H), 3.75 (s, 3H), 2.91-3.15 (m, 6H), 2.55-2.81 (m, 9H)

EXAMPLE 37

Synthesis of 3-{2-[4-(4-methoxyphenyl)piperazin-1-yl]ethyl}aminomethyl-5-methyl-1-phenylpyrazole [Compound 37]

Compound 37 was prepared using the same method as that of Example 1 except that 4-(4-methoxyphenyl)piperazin-1-ylethylamine and 5-methyl-1-phenylpyrazole-3-carbaldehyde were used.

Yield: 22.1%

$^1$H NMR (300 MHz, CDCl$_3$) δ 7.53 (d, J=7.2 Hz, 2H), 7.45 (t, J=7.5 Hz, 2H), 7.37 (d, J=7.3 Hz, 1H), 6.83-6.92 (m, 4H), 6.20 (s, 1H), 3.85 (s, 2H), 3.78 (s, 3H), 3.07 (t, J=4.7 Hz, 4H), 2.73 (t, J=5.9 Hz, 2H), 2.52-2.60 (m, 6H), 2.33 (s, 3H)

EXAMPLE 38

Synthesis of 1-t-butyl-3-{2-[4-(4-methoxyphenyl)piperazin-1-yl]ethyl}aminomethyl-5-propylpyrazole [Compound 38]

Compound 38 was prepared using the same method as that of Example 1 except that 4-(4-methoxyphenyl)piperazin-1-ylethylamine and 5-propyl-1-t-butylpyrazole-3-carbaldehyde were used.

Yield: 34.2%

$^1$H NMR (300 MHz, CDCl$_3$) δ 6.83-6.92 (m, 4H), 6.04 (s, 1H), 3.96 (s, 2H), 3.77 (s, 3H), 3.09 (m, 4H), 2.82 (t, J=5.6 Hz, 2H), 2.52-2.62 (m, 6H), 2.45 (m, 2H), 1.41-1.68 (m, 11H), 0.95 (t, J=7.3 Hz, 3H)

EXAMPLE 39

Synthesis of 3-{2-[4-(4-methoxyphenyl)piperazin-1-yl]ethyl}aminomethyl-5-propyl-1-phenylpyrazole [Compound 39]

Compound 39 was prepared using the same method as that of Example 1 except that 4-(4-methoxyphenyl)piperazin-1-ylethylamine and 5-propyl-1-phenylpyrazole-3-carbaldehyde were used.

Yield: 41.3%

$^1$H NMR (300 MHz, CDCl$_3$) δ 7.39-7.46 (m, 5H), 6.82-6.85 (m, 4H), 6.24 (s, 1H), 3.04 (m, 4H), 2.91 (t, J=5.6 Hz, 2H), 2.57-2.77 (m, 8H), 1.60 (m, 2H), 0.92 (t, J=7.3 Hz, 3H)

EXAMPLE 40

Synthesis of 1-t-butyl-5-iso-butyl-3-{2-[4-(4-methoxyphenyl)piperazin-1-yl]ethyl}aminomethylpyrazole [Compound 40]

Compound 40 was prepared using the same method as that of Example 1 except that 4-(4-methoxyphenyl)piperazin-1-ylethylamine and 1-t-butyl-5-iso-butylpyrazole-3-carbaldehyde were used.

Yield: 35.2%

$^1$H NMR (300 MHz, CDCl$_3$) δ 6.55-6.59 (m, 4H), 6.17 (s, 1H), 3.96 (s, 2H), 3.76 (s, 3H), 2.91-3.16 (m, 6H), 2.52-2.78 (m, 8H), 1.98 (m, 1H), 1.60 (s, 9H), 0.98 (d, J=6.3 Hz, 6H)

EXAMPLE 41

Synthesis of 2-t-butyl-5-iso-butyl-3-{2-[4-(4-methoxyphenyl)piperazin-1-yl]ethyl}aminomethylpyrazole [Compound 41]

Compound 41 was prepared using the same method as that of Example 1 except that 4-(4-methoxyphenyl)piperazin-1-ylethylamine and 2-t-butyl-5-iso-butylpyrazole-3-carbaldehyde were used.

Yield: 29.7%

$^1$H NMR (300 MHz, CDCl$_3$) δ 6.75-6.92 (m, 4H), 6.01 (s, 1H), 3.96 (s, 2H), 3.77 (s, 3H), 3.09 (t, J=4.6 Hz, 4H), 2.81 (t, J=5.8 Hz, 2H), 2.57-2.68 (m, 6H), 2.43 (d, J=7.1 Hz, 2H), 1.89 (m, 1H), 1.62 (s, 9H), 0.93 (d, J=6.6 Hz, 6H)

EXAMPLE 42

Synthesis of 5-iso-butyl-3-{2-[4-(4-methoxyphenyl)piperazin-1-yl]ethyl}aminomethyl-1-phenyl pyrazole [Compound 42]

Compound 42 was prepared using the same method as that of Example 1 except that 4-(4-methoxyphenyl)piperazin-1-ylethylamine and 5-iso-butyl-1-phenylpyrazole-3-carbaldehyde were used.

Yield: 24.2%

$^1$H NMR (300 MHz, CDCl$_3$) δ 7.30-7.55 (m, 5H), 6.69-6.94 (m, 4H), 6.24 (s, 1H), 3.97 (s, 2H), 3.76 (s, 3H), 3.03 (m, 4H), 2.92 (m, 2H), 2.56-2.77 (m, 6H), 2.50 (d, J=6.9 Hz, 2H), 1.82 (m, 1H), 0.86 (d, J=6.3 Hz, 6H)

EXAMPLE 43

Synthesis of 5-(furan-2-yl)-3-{2-[4-(4-methoxyphenyl)piperazin-1-yl]ethyl}aminomethyl-1-phenyl pyrazole [Compound 43]

Compound 43 was prepared using the same method as that of Example 1 except that 4-(4-methoxyphenyl)piperazin-1-ylethylamine and 1-phenyl-5-(2-furyl)pyrazole-3-carbaldehyde were used.

Yield: 74.1%

$^1$H NMR (300 MHz, CDCl$_3$) δ 7.21-7.53 (m, 6H), 6.74-6.91 (m, 4H), 6.72 (s, 1H), 6.30 (m, 1H), 5.95 (m, 1H), 3.99 (s, 2H), 3.82 (s, 3H), 3.71 (m, 4H), 3.11 (m, 4H), 2.85 (m, 2H), 2.76 (m, 2H)

EXAMPLE 44

Synthesis of 3-{2-[4-(4-methoxyphenyl)piperazin-1-yl]ethyl}aminomethyl-1,5-phenylpyrazole [Compound 44]

Compound 44 was prepared using the same method as that of Example 1 except that 4-(4-methoxyphenyl)piperazin-1-ylethylamine and 1,5-diphenylpyrazole-3-carbaldehyde were used.

Yield: 47.1%

$^1$H NMR (300 MHz, CDCl$_3$) δ 7.25-7.37 (m, 8H), 7.23 (m, 2H), 6.78-6.87 (m, 4H), 6.60 (s, 1H), 4.09 (s, 2H), 3.77 (s, 3H), 3.01 (m, 6H), 2.70 (t, J=5.8 Hz, 2H), 2.63 (m, 4H)

EXAMPLE 45

Synthesis of 1-t-butyl-5-(4-methylphenyl)-3-{2-[4-(4-methoxyphenyl)piperazin-1-yl]ethyl}aminomethylpyrazole [Compound 45]

Compound 45 was prepared using the same method as that Example 1 except that 4-(4-methoxyphenyl)piperazin-1-yl-ethylamine and 1-t-butyl-5-(4-methylphenyl)pyrazole-3-carbaldehyde were used.

Yield: 95.9%

$^1$H NMR (300 MHz, CDCl$_3$) δ 7.04-7.25 (m, 4H), 6.72-6.94 (m, 4H), 6.45 (s, 1H), 4.07 (s, 2H), 3.69 (s, 3H), 2.53-3.55 (m, 12H), 2.39 (s, 3H), 1.42 (s, 9H)

EXAMPLE 46

Synthesis of 1-t-butyl-5-(4-chlorophenyl)-3-{2-[4-(4-methoxyphenyl)piperazin-1-yl]ethyl}aminomethylpyrazole [Compound 46]

Compound 46 was prepared using the same method as that of Example 1 except that 4-(4-methoxyphenyl)piperazin-1-ylethylamine and 5-(4-chlorophenyl)-1-t-butylpyrazole-3-carbaldehyde were used.

Yield: 86.0%

$^1$H NMR (300 MHz, CDCl$_3$) δ 7.14-7.43 (m, 4H), 6.69-6.94 (m, 4H), 6.14 and 6.06 (s, 1H), 4.20 and 4.07 (s, 2H), 3.74 (s, 3H), 2.45-3.42 (m, 12H), 1.40 (s, 9H)

EXAMPLE 47

Synthesis of 5-(4-cyclohexyl phenyl)-3-{2-[4-(4-methoxyphenyl)piperazin-1-yl]ethyl}aminomethyl-1-phenyl pyrazole [Compound 47]

Compound 47 was prepared using the same method as that of Example 1 except that 4-(4-methoxyphenyl)piperazin-1-ylethylamine and 5-(4-cyclohexylphenyl)-1-phenylpyrazole-3-carbaldehyde were used.

Yield: 89.1%

$^1$H NMR (300 MHz, CDCl$_3$) δ 7.17-7.41 (m, 5H), 6.96-7.15 (m, 4H), 6.66-6.90 (m, 4H), 6.46 (s, 1H), 4.04 (s, 2H), 3.87 (s, 3H), 2.55-3.40 (m, 12H), 2.46 (m, 1H), 1.64-1.95 (m, 6H), 1.37 (m, 4H)

EXAMPLE 48

Synthesis of 3-{2-[4-(4-methoxyphenyl)piperazin-1-yl]ethyl}aminomethyl-1-phenyl-5-(4-piperidin-1-yl)phenylpyrazole [Compound 48]

Compound 48 was prepared using the same method as that of Example 1 except that 4-(4-methoxyphenyl)piperazin-1-ylethylamine and 1-phenyl-5-(4-(piperidin-1-yl)phenyl)pyrazole-3-carbaldehyde were used.

Yield: 88.9%

$^1$H NMR (300 MHz, CDCl$_3$) δ 7.17-7.44 (m, 5H), 6.98-7.15 (m, 2H), 6.88-6.69 (m, 6H), 6.59 and 6.46 (s, 1H), 4.89 (brs, 1H), 4.18 and 3.90 (s, 2H), 3.75 (s, 3H), 3.13 (m, 4H), 2.99 (m, 2H), 2.72 (m, 4H), 2.61 (m, 2H), 1.44-1.81 (m, 6H), 1.26 (m, 4H)

EXAMPLE 49

Synthesis of 5-methyl-3-{2-[4-(4-nitrophenyl)piperazin-1-yl]ethyl}aminomethyl-1-phenylpyrazole [Compound 49]

Compound 49 was prepared using the same method as that of Example 1 except that 4-(4-nitrophenyl)piperazin-1-yl-ethylamine and 5-methyl-1-phenylpyrazole-3-carbaldehyde were used.

Yield: 59.6%

$^1$H NMR (300 MHz, CDCl$_3$) δ 8.11 (d, J=9.3 Hz, 2H), 7.23-7.56 (m, 5H), 6.76 (m, 2H), 6.28 and 6.20 (s, 1H), 4.04 and 3.84 (s, 2H), 3.34 (m, 4H), 2.97 (m, 2H), 2.70 (t, J=5.6 Hz, 2H), 2.60 (m, 4H), 2.33 (s, 3H)

EXAMPLE 50

Synthesis of 1-t-butyl-3-{2-[4-(4-nitrophenyl)piperazin-1-yl]ethyl}aminomethyl-5-propylpyrazole [Compound 50]

Compound 50 was prepared using the same method as that of Example 1 except that 4-(4-nitrophenyl)piperazin-1-yl-ethylamine and 5-propyl-1-t-butylpyrazole-3-carbaldehyde were used.

Yield: 95.6%

$^1$H NMR (300 MHz, CDCl$_3$) δ 8.12 (d, J=9.4 Hz, 2H), 6.82 (d, J=9.4 Hz, 2H), 6.02 (s, 1H), 3.95 (s, 2H), 3.42 (t, J=5.0 Hz, 4H), 2.81 (t, J=5.8 Hz, 2H), 2.55-2.66 (m, 6H), 2.53 (m, 2H), 1.54-1.71 (m, 11H), 0.94 (t, J=7.4 Hz, 3H)

EXAMPLE 51

Synthesis of 3-{2-[4-(4-nitrophenyl)piperazin-1-yl]ethyl}aminomethyl-1-phenyl-5-propylpyrazole [Compound 51]

Compound 51 was prepared using the same method as that of Example 1 except that 4-(4-nitrophenyl)piperazin-1-yl-ethylamine and 5-propyl-1-phenylpyrazole-3-carbaldehyde were used.

Yield: 78.6%

$^1$H NMR (300 MHz, CDCl$_3$) δ 8.09 (d, J=9.3 Hz, 2H), 7.31-7.55 (m, 5H), 6.76 (d, J=9.4 Hz, 2H), 6.23 (s, 1H), 3.94 (s, 2H), 3.36 (t, J=4.7 Hz, 4H), 2.88 (t, J=5.8 Hz, 4H), 2.47-2.71 (m, 6H), 1.61 (m, 2H), 0.97 (t, J=7.3 Hz, 3H)

EXAMPLE 52

Synthesis of 1-t-butyl-5-iso-butyl-3-{2-[4-(4-nitrophenyl)piperazin-1-yl]ethyl}aminomethylpyrazole [Compound 52]

Compound 52 was prepared using the same method as that of Example 1 except that 4-(4-nitrophenyl)piperazin-1-yl-ethylamine and 1-t-butyl-5-iso-butylpyrazole-3-carbaldehyde were used.

Yield: 74.5%

$^1$H NMR (300 MHz, CDCl$_3$) δ 8.11 (d, J=9.3 Hz, 2H), 6.81 (d, J=9.3 Hz, 2H), 5.95 (s, 1H), 3.95 (s, 2H), 3.41 (t, J=4.7 Hz, 4H), 2.81 (t, J=5.7 Hz, 2H), 2.54-2.68 (m, 6H), 2.43 (d, J=7.1 Hz, 2H), 1.88 (m, 1H), 1.62 (s, 9H), 0.92 (d, J=6.6 Hz, 6H)

EXAMPLE 53

Synthesis of 5-iso-butyl-3-{2-[4-(4-nitrophenyl)piperazin-1-yl]ethyl}aminomethyl-1-phenylpyrazole [Compound 53]

Compound 53 was prepared using the same method as that of Example 1 except that 4-(4-nitrophenyl)piperazin-1-yl-ethylamine and 5-iso-butyl-1-phenylpyrazole-3-carbaldehyde were used.

Yield: 79.3%

$^1$H NMR (300 MHz, CDCl$_3$) δ 8.09 (d, J=9.2 Hz, 2H), 7.33-7.54 (m, 5H), 6.75 (d, J=9.2 Hz, 2H), 6.22 and 6.17 (s, 1H), 3.94 and 3.81 (s, 2H), 3.36 (m, 4H), 2.89 (t, J=5.5 Hz, 2H), 2.54-2.75 (m, 6H), 2.50 (d, J=7.0 Hz, 2H), 1.81 (m, 1H), 0.86 (d, J=6.5 Hz, 6H)

EXAMPLE 54

Synthesis of 5-(furan-2-yl)-3-{2-[4-(4-nitrophenyl)piperazin-1-yl]ethyl}aminomethyl-1-phenylpyrazole [Compound 54]

Compound 54 was prepared using the same method as that of Example 1 except that 4-(4-nitrophenyl)piperazin-1-yl-ethylamine and 1-phenyl-5-(2-furyl)pyrazole-3-carbaldehyde were used.

Yield: 93.3%

$^1$H NMR (300 MHz, CDCl$_3$) δ 8.08 (m, 2H), 7.31-7.52 (m, 6H), 6.79 (s, 1H), 6.70 (m, 2H), 6.33 (m, 1H), 6.95 (m, 1H), 4.14 (s, 2H), 3.89 (m, 2H), 3.35 (m, 4H), 2.70 (m, 2H), 2.58 (m, 4H)

EXAMPLE 55

Synthesis of 1,5-diphenyl-3-{2-[4-(4-nitrophenyl)piperazin-1-yl]ethyl}aminomethylpyrazole [Compound 55]

Compound 55 was prepared using the same method as that of Example 1 except that 4-(4-nitrophenyl)piperazin-1-yl-ethylamine and 1,5-diphenylpyrazole-3-carbaldehyde were used.

Yield: 68.5%

$^1$H NMR (300 MHz, CDCl$_3$) δ 8.10 (d, J=9.3 Hz, 2H), 7.25-7.39 (m, 8H), 7.23 (m, 2H), 6.75 (d, J=9.4 Hz, 2H), 6.55 (s, 1H), 4.02 (s, 2H), 3.36 (t, J=4.7 Hz, 4H), 2.95 (t, J=5.8 Hz, 2H), 2.66 (t, J=5.8 Hz, 2H), 2.60 (t, J=4.7 Hz, 4H)

EXAMPLE 56

Synthesis of 1-t-butyl-5-(4-methylphenyl)-3-{2-[4-(4-nitrophenyl)piperazin-1-yl]ethyl}aminomethylpyrazole [Compound 56]

Compound 56 was prepared using the same method as that of Example 1 except that 4-(4-nitrophenyl)piperazin-1-yl-ethylamine and 1-t-butyl-5-(4-methylphenyl)pyrazole-3-carbaldehyde were used.

Yield: 69.4%

$^1$H NMR (300 MHz, CDCl$_3$) δ 8.09 (d, J=7.6 Hz, 2H), 7.11-7.24 (m, 4H), 6.76 (d, J=8.2 Hz, 2H), 6.30 and 6.11 (s, 1H), 4.20 and 3.94 (s, 2H), 3.40 (m, 4H), 2.83 (m, 2H), 2.54-2.75 (m, 6H), 2.41 (s, 3H), 1.42 (s, 9H)

EXAMPLE 57

Synthesis of 1-t-butyl-5-(4-chlorophenyl)-3-{2-[4-(4-nitrophenyl)piperazin-1-yl]ethyl}aminomethylpyrazole [Compound 57]

Compound 57 was prepared using the same method as that of Example 1 except that 4-(4-nitrophenyl)piperazin-1-yl-ethylamine and 5-(4-chlorophenyl)-1-t-butylpyrazole-3-carbaldehyde were used.

Yield: 50.4%

$^1$H NMR (300 MHz, CDCl$_3$) δ 8.09 (d, J=8.9 Hz, 2H), 7.37 (m, 2H), 7.26 (m, 2H), 6.78 (d, J=8.9 Hz, 2H), 6.17 and 6.07 (s, 1H), 4.08 and 3.71 (s, 2H), 3.52 (m, 4H), 2.51-3.16 (m, 8H), 1.42 (s, 9H)

EXAMPLE 58

Synthesis of 5-(4-cyclohexylphenyl)-3-{2-[4-(4-nitrophenyl)piperazin-1-yl]ethyl}aminomethyl-1-phenylpyrazole [Compound 58]

Compound 58 was prepared using the same method as that of Example 1 except that 4-(4-nitrophenyl)piperazin-1-yl-ethylamine and 5-(4-cyclohexyphenyl)-1-phenylpyrazole-3-carbaldehyde were used.

Yield: 78.1%

$^1$H NMR (300 MHz, CDCl$_3$) δ 8.05 (d, J=9.0 Hz, 2H), 7.19-7.42 (m, 5H), 6.99-7.16 (m, 4H), 6.69 (d, J=9.2 Hz, 2H), 6.59 (s, 1H), 4.06 (s, 2H), 3.38 (m, 4H), 2.78-3.15 (m, 4H), 2.69 (m, 4H), 2.47 (m, 1H), 1.65-1.94 (m, 6H), 1.34 (m, 4H)

EXAMPLE 59

Synthesis of 1-phenyl-5-(4-piperidin-1-yl)phenyl-3-{2-[4-(4-nitrophenyl)piperazin-1-yl]ethyl}aminomethylpyrazole [Compound 59]

Compound 59 was prepared using the same method as that of Example 1 except that 4-(4-nitrophenyl)piperazin-1-yl-ethylamine and 1-phenyl-5-(4-(piperidin-1-yl)phenyl)pyrazole-3-carbaldehyde were used.

Yield: 81.5%

$^1$H NMR (300 MHz, CDCl$_3$) δ 8.05 (d, J=9.0 Hz, 2H), 7.24-7.43 (m, 5H), 7.05 (d, J=8.5 Hz, 2H), 6.78 (d, J=8.6 Hz, 2H), 6.66 (d, J=9.3 Hz, 2H), 6.55 (s, 1H), 4.06 (s, 2H), 3.36 (m, 4H), 3.06-3.39 (m, 6H), 2.98 (m, 2H), 2.57 (m, 4H), 1.45-1.75 (m, 6H)

EXAMPLE 60

Synthesis of 3-{2-[4-(2-fluorophenyl)piperazin-1-yl]ethyl}aminomethyl-5-20 methylpyrazole [Compound 60]

Compound 60 was prepared using the same method as that of Example 1 except that 4-(2-fluorophenyl)piperazin-1-yl-ethylamine and 5-methylpyrazole-3-carbaldehyde were used.

Yield: 39.4%

$^1$H NMR (300 MHz, CDCl$_3$) δ 7.02-7.10 (m, 2H), 6.86-7.01 (m, 2H), 6.16 (s, 1H), 3.99 (s, 2H), 3.08 (m, 4H), 3.00 (t, J=5.5 Hz, 2H), 2.73 (t, J=6.7 Hz, 4H), 2.58-2.69 (m, 5H)

EXAMPLE 61

Synthesis of 3-{2-[4-(2-fluorophenyl)piperazin-1-yl]ethyl}aminomethyl-5-methyl-1-phenylpyrazole [Compound 61]

Compound 61 was prepared using the same method as that of Example 1 except that 4-(2-fluorophenyl)piperazin-1-yl-ethylamine and 5-methyl-1-phenylpyrazole-3-carbaldehyde were used.

Yield: 87.4%

$^1$H NMR (300 MHz, CDCl$_3$) δ 7.52 (m, 2H), 7.44 (m, 2H), 7.36 (d, J=6.5 Hz, 1H), 7.04 (d, J=6.8 Hz, 1H), 6.83-6.99 (m, 3H), 6.19 (s, 1H), 3.83 (s, 2H), 3.06 (m, 4H), 2.70 (m, 2H), 2.41-2.66 (m, 6H), 2.23 (s, 3H)

EXAMPLE 62

Synthesis of 1-t-butyl-3-{2-[4-(2-fluorophenyl)piperazin-1-yl]ethyl}aminomethyl-5-propyl pyrazole [Compound 62]

Compound 62 was prepared using the same method as Example 1 except that 4-(2-fluorophenyl)piperazin-1-ylethylamine and 5-propyl-1-t-butylpyrazole-3-carbaldehyde were used.

Yield: 76.7%

$^1$H NMR (300 MHz, CDCl$_3$) δ 6.98 (m, 1H), 6.78-6.93 (m, 3H), 5.96 (s, 1H), 3.87 (s, 2H), 3.03 (m, 4H), 2.73 (t, J=5.7 Hz, 2H), 2.48-2.62 (m, 6H), 2.45 (d, J=7.9 Hz, 2H), 1.43-1.65 (m, 11H), 0.88 (t, J=7.3 Hz, 3H)

EXAMPLE 63

Synthesis of 3-{2-[4-(2-fluorophenyl)piperazin-1-yl]ethyl}aminomethyl-1-phenyl-5-propylpyrazole [Compound 63]

Compound 63 was prepared using the same method as that of Example 1 except that 4-(2-fluorophenyl)piperazin-1-yl-ethylamine and 5-propyl-1-phenylpyrazole-3-carbaldehyde were used.

Yield: 59.3%

$^1$H NMR (300 MHz, CDCl$_3$) δ 7.25-7.62 (m, 5H), 7.02 (d, J=7.3 Hz, 1H), 6.74-6.99 (m, 3H), 6.28 (s, 1H), 4.15 (brs, 1H), 3.99 (s, 2H), 3.05 (m, 4H), 2.94 (m, 2H), 2.43-2.76 (m, 8H), 1.59 (m, 2H), 0.91 (m, 3H)

EXAMPLE 64

Synthesis of 1-t-butyl-5-iso-butyl-3-{2-[4-(2-fluorophenyl)piperazin-1-yl]ethyl}aminomethylpyrazole [Compound 64]

Compound 64 was prepared using the same method as that of Example 1 except that 4-(2-fluorophenyl)piperazin-1-yl-ethylamine and 1-t-butyl-5-iso-butylpyrazole-3-carbaldehyde were used.

Yield: 76.7%

$^1$H NMR (300 MHz, CDCl$_3$) δ 7.01-7.09 (m, 2H), 6.87-7.00 (m, 2H), 6.01 (s, 1H), 3.95 (s, 2H), 3.11 (m, 4H), 2.81 (t, J=5.9 Hz, 2H), 2.55-2.68 (m, 6H), 2.44 (d, J=7.1 Hz, 2H), 1.87 (m, 1H), 1.63 (s, 9H), 0.93 (d, J=6.6 Hz, 6H)

EXAMPLE 65

Synthesis of 2-t-butyl-5-iso-butyl-3-{2-[4-(2-fluorophenyl)piperazin-1-yl]ethyl}aminomethylpyrazole [Compound 65]

Compound 65 was prepared using the same method as that of Example 1 except that 4-(2-fluorophenyl)piperazin-1-yl-ethylamine and 2-t-butyl-5-iso-butylpyrazole-3-carbaldehyde were used.

Yield: 60.2%

$^1$H NMR (300 MHz, CDCl$_3$) δ 6.83-7.17 (m, 4H), 6.18 (s, 1H), 5.93 (brs, 1H), 3.99 (s, 2H), 3.06 (m, 4H), 2.95 (m, 2H), 2.52-2.83 (m, 8H), 1.97 (m, 1H), 1.57 (s, 9H), 0.95 (m, 6H)

EXAMPLE 66

Synthesis of 5-iso-butyl-3-{2-[4-(2-fluorophenyl)piperazin-1-yl]ethyl}aminomethyl-1-phenylpyrazole [Compound 66]

Compound 66 was prepared using the same method as that of Example 1 except that 4-(2-fluorophenyl)piperazin-1-yl-ethylamine and 5-iso-butyl-1-phenylpyrazole-3-carbaldehyde were used.

Yield: 71.8%

$^1$H NMR (300 MHz, CDCl$_3$) δ 7.44 (m, 2H), 7.40 (m, 3H), 7.01 (m, 1H), 6.92 (m, 3H), 6.21 (s, 1H), 3.93 (s, 2H), 3.07 (m, 4H), 2.89 (t, J=6.0 Hz, 2H), 2.58-2.74 (m, 6H), 2.51 (d, J=6.1 Hz, 2H), 1.83 (m, 1H), 0.87 (d, J=6.6 Hz, 6H)

EXAMPLE 67

Synthesis of 3-{2-[4-(2-fluorophenyl)piperazin-1-yl]ethyl}aminomethyl-5-(furan-2-yl)-1-phenylpyrazole [Compound 67]

Compound 67 was prepared using the same method as that of Example 1 except that 4-(2-fluorophenyl)piperazin-1-yl-ethylamine and 1-phenyl-5-(2-furyl)pyrazole-3-carbaldehyde were used.

Yield: 86.3%

$^1$H NMR (300 MHz, CDCl$_3$) δ 7.41-7.52 (m, 4H), 7.38 (m, 1H), 6.86-7.13 (m, 5H), 6.68 (s, 1H), 6.33 (m, 1H), 5.96 (m, 1H), 3.97 (s, 2H), 3.08 (m, 4H), 2.90 (t, J=5.8 Hz, 2H), 2.51-2.73 (m, 6H)

EXAMPLE 68

Synthesis of 1,5-diphenyl-3-{2-[4-(2-fluorophenyl)piperazin-1-yl]ethyl}aminomethylpyrazole [Compound 68]

Compound 68 was prepared using the same method as that of Example 1 except that 4-(2-fluorophenyl)piperazin-1-yl-ethylamine and 1,5-diphenylpyrazole-3-carbaldehyde were used.

Yield: 74.5%

$^1$H NMR (300 MHz, CDCl$_3$) δ 7.18-7.37 (m, 10H), 6.83-7.08 (m, 4H), 6.59 (s, 1H), 4.49 (brs, 1H), 4.07 (s, 2H), 3.06 (m, 4H), 2.99 (m, 2H), 2.59-2.69 (m, 6H)

EXAMPLE 69

Synthesis of 1-t-butyl-3-{2-[4-(2-fluorophenyl)piperazin-1-yl]ethyl}aminomethyl-5-(4-methylphenyl)pyrazole [Compound 69]

Compound 69 was prepared using the same method as that of Example 1 except that 4-(2-fluorophenyl)piperazin-1-yl-ethylamine and 1-t-butyl-5-(4-methylphenyl)pyrazole-3-carbaldehyde were used.

Yield: 89.4%

$^1$H NMR (300 MHz, CDCl$_3$) δ 7.12-7.24 (m, 5H), 6.86-7.09 (m, 5H), 6.19 (s, 1H), 4.31 (brs, 1H), 4.05 (s, 2H), 3.10 (m, 4H), 3.03 (t, J=5.8 Hz, 2H), 2.75 (t, J=5.8 Hz, 2H), 2.67 (m, 4H), 2.40 (s, 3H), 1.43 (s, 9H)

EXAMPLE 70

Synthesis of 1-t-butyl-5-(4-chlorophenyl)-3-{2-[4-(2-fluorophenyl)piperazin-1-yl]ethyl}aminomethylpyrazole [Compound 70]

Compound 70 was prepared using the same method as that of Example 1 except that 4-(2-fluorophenyl)piperazin-1-yl-ethylamine and 5-(4-chlorophenyl)-1-t-butylpyrazole-3-carbaldehyde were used.

Yield: 74.2%

$^1$H NMR (300 MHz, CDCl$_3$) δ 7.35 (d, J=8.2 Hz, 2H), 7.25 (d, J=8.3 Hz, 2H), 7.01-7.12 (m, 2H), 6.87-6.99 (m, 2H), 6.17 (s, 1H), 3.97 (s, 2H), 3.10 (m, 4H), 2.96 (t, J=5.8 Hz, 2H), 2.56-2.79 (m, 6H), 1.43 (s, 9H)

EXAMPLE 71

Synthesis of 5-(4-cyclohexylphenyl)-3-{2-[4-(2-fluorophenyl)piperazin-1-yl]ethyl}aminomethyl-1-phenylpyrazole [Compound 71]

Compound 71 was prepared using the same method as that of Example 1 except that 4-(2-fluorophenyl)piperazin-1-yl-ethylamine and 5-(4-cyclohexylphenyl)-1-phenyl pyrazole-3-carbaldehyde were used.

Yield: 64.8%

$^1$H NMR (300 MHz, CDCl$_3$) δ 7.24-7.39 (m, 5H), 7.08-7.17 (m, 4H), 7.01-7.07 (m, 2H), 6.83-6.99 (m, 3H), 6.52 and 6.47 (s, 1H), 4.02 and 3.82 (s, 2H), 3.06 (m, 4H), 2.96 (t, J=5.8 Hz, 2H), 2.55-2.80 (m, 6H), 2.48 (m, 1H), 1.68-1.94 (m, 6H), 1.38 (t, J=9.9 Hz, 4H)

EXAMPLE 72

Synthesis of 3-{2-[4-(2-fluorophenyl)piperazin-1-yl]ethyl}aminomethyl-1-phenyl-5-(4-piperidin-1-yl)phenylpyrazole [Compound 72]

Compound 72 was prepared using the same method as that of Example 1 except that 4-(2-fluorophenyl)piperazin-1-yl-ethylamine and 1-phenyl-5-(4-(piperidin-1-yl)phenyl)pyrazole-3-carbaldehyde were used.

Yield: 74.3% tk $^1$H NMR (300 MHz, CDCl$_3$) δ 7.28-7.37 (m, 5H), 6.77-7.11 (m, 8H), 6.48 (s, 1H), 4.04 (s, 2H), 3.18 (t, J=5.1 Hz, 4H), 3.05 (m, 4H), 2.98 (t, J=5.9 Hz, 2H), 2.69 (m, 2H), 2.64 (m, 4H), 1.54-1.75 (m, 6H)

EXAMPLE 73

Synthesis of 3-{2-[4-(3-chlorophenyl)piperazin-1-yl]ethyl}aminomethyl-5-methylpyrazole [Compound 73]

Compound 73 was prepared using the same method as that of Example 1 except that 4-(3-chlorophenyl)piperazin-1-yl-ethylamine and 5-methylpyrazole-3-carbaldehyde were used.

Yield: 60.4%

$^1$H NMR (300 MHz, CDCl$_3$) δ 7.16 (t, J=8.1 Hz, 1H), 6.73-6.87 (m, 3H), 6.17 (s, 1H), 4.90 (brs, 1H), 3.99 (s, 2H), 3.17 (m, 4H), 3.00 (t, J=5.8 Hz, 2H), 2.73 (m, 4H), 2.60 (m, 2H), 2.04 (2, 3H)

EXAMPLE 74

Synthesis of 3-{2-[4-(3-chlorophenyl)piperazin-1-yl]ethyl}aminomethyl-5-methyl-1-phenylpyrazole [Compound 74]

Compound 74 was prepared using the same method as Example 1 except that 4-(3-chlorophenyl)piperazin-1-yl-ethylamine and 5-methyl-1-phenylpyrazole-3-carbaldehyde were used.

Yield: 65.4%

$^1$H NMR (300 MHz, CDCl$_3$) δ 7.49 (m, 3H), 7.39 (m, 2H), 7.12 (t, J=7.8 Hz, 1H), 6.79 (d, J=7.2 Hz, 1H), 6.67 (m, 2H), 6.51 (s, 1H), 4.32 (s, 2H), 3.19 (m, 2H), 3.03 (m, 4H), 2.84 (m, 2H), 2.59 (m, 4H), 2.31 (s, 3H)

EXAMPLE 75

Synthesis of 1-t-butyl-3-{2-[4-(3-chlorophenyl)piperazin-1-yl]ethyl}aminomethyl-5-propyl pyrazole [Compound 75]

Compound 75 was prepared using the same method as that of Example 1 except that 4-(3-chlorophenyl)piperazin-1-yl-ethylamine and 5-propyl-1-t-butylpyrazole-3-carbaldehyde were used.

Yield: 76.5%

$^1$H NMR (300 MHz, CDCl$_3$) δ 7.26 (s, 2H), 7.16 (t, J=8.1 Hz, 1H), 6.74-6.92 (m, 3H), 6.03 (s, 1H), 3.18 (t, J=5.0 Hz, 4H), 2.80 (t, J=5.9 Hz, 2H), 2.54-2.64 (m, 6H), 2.52 (m, 2H)

EXAMPLE 76

Synthesis of 3-{2-[4-(3-chlorophenyl)piperazin-1-yl]ethyl}aminomethyl-1-phenyl-5-propylpyrazole [Compound 76]

Compound 75 was prepared using the same method as that of Example 1 except that 4-(3-chlorophenyl)piperazin-1-yl-ethylamine and 5-propyl-1-phenylpyrazole-3-carbaldehyde were used.

Yield: 48.5%

$^1$H NMR (300 MHz, CDCl$_3$) δ 7.32-7.53 (m, 5H), 7.15 (t, J=8.1 Hz, 1H), 6.71-6.90 (m, 3H), 6.32 (s, 1H), 3.89 (s, 2H), 3.18 (m, 4H), 2.83 (m, 2H), 2.51-2.74 (m, 8H), 1.65 (m, 2H), 0.94 (t, J=7.4 Hz, 3H)

EXAMPLE 77

Synthesis of 1-t-butyl-5-iso-butyl-3-{2-[4-(3-chlorophenyl)piperazin-1-yl]ethyl}aminomethylpyrazole [Compound 77]

Compound 77 was prepared using the same method as that of Example 1 except that 4-(3-chlorophenyl)piperazin-1-ylethylamine and 1-t-butyl-5-iso-butylpyrazole-3-carbaldehyde were used.

Yield: 77.7%

$^1$H NMR (300 MHz, CDCl$_3$) δ 7.20 (t, J=7.8 Hz, 1H), 6.90 (s, 1H), 6.82 (m, 2H), 6.0 (s, 1H), 3.99 (s, 2H), 3.22 (m, 4H), 2.84 (m, 2H), 2.52-2.74 (m, 6H), 2.46 (d, J=6.9 Hz, 2H), 1.92 (m, 1 HO, 1.65 (s, 9H), 0.96 (d, J=6.3 Hz, 6H)

EXAMPLE 78

Synthesis of 2-t-butyl-5-iso-butyl-3-{2-[4-(3-chlorophenyl)piperazin-1-yl]ethyl}aminomethylpyrazole [Compound 78]

Compound 78 was prepared using the same method as that of Example 1 except that 4-(3-chlorophenyl)piperazin-1-ylethylamine and 2-t-butyl-5-iso-butylpyrazole-3-carbaldehyde were used.

Yield: 54.8%

$^1$H NMR (300 MHz, CDCl$_3$) δ 7.16 (t, J=8.1 Hz, 1H), 6.87 (s, 1H), 6.60 (m, 2H), 6.00 (s, 1H), 3.95(s, 2H), 3.18 (m, 4H), 2.80 (t, J=5.7 Hz, 2H), 2.51-2.67 (m, 6H), 2.44 (d, J=7.1 Hz, 2H), 1.90 (m, 1H), 1.63 (s, 9H), 0.93 (d, J=6.6 Hz, 6H)

EXAMPLE 79

Synthesis of 5-iso-butyl-3-{2-[4-(3-chlorophenyl)piperazin-1-yl]ethyl}aminomethyl-1-phenylpyrazole [Compound 79]

Compound 79 was prepared using the same method as that of Example 1 except that 4-(3-chlorophenyl)piperazin-1-ylethylamine and 5-iso-butyl-1-phenylpyrazole-3-carbaldehyde were used.

Yield: 47.7%

$^1$H NMR (300 MHz, CDCl$_3$) δ 7.31-7.58 (m, 5H), 7.14 (t, J=8.1 Hz, 1H), 6.80 (m, 2H), 6.68-6.78 (m, 2H), 6.21 (s, 1H), 3.94 (s, 2H), 3.12 (m, 4H), 2.89 (t, J=5.7 Hz, 2H), 2.52-2.69 (m, 6H), 2.51 (d, J=7.5 Hz, 2H), 1.82 (m, 1H), 1.26 (s, 9H), 0.87 (d, J=6.6 Hz, 6H)

EXAMPLE 80

Synthesis of 3-{2-[4-(3-chlorophenyl)piperazin-1-yl]ethyl}aminomethyl-5-(furan-2-yl)-1-phenylpyrazole [Compound 80]

Compound 80 was prepared using the same method as that of Example 1 except that 4-(3-chlorophenyl)piperazin-1-ylethylamine and 1-phenyl-5-(2-furyl)pyrazole-3-carbaldehyde were used.

Yield: 68.6%

$^1$H NMR (300 MHz, CDCl$_3$) δ 7.32-7.56 (m, 6H), 7.13 (t, J=7.8 Hz, 1H), 6.71-6.90 (m, 3H), 6.67 (s, 1H), 6.33 (m, 1H), 5.97 (m, 1H), 3.99 (s, 2H), 3.13 (m, 4H), 2.90 (m, 2H), 2.48-2.71 (m, 6H)

EXAMPLE 81

Synthesis of 3-{2-[4-(4-diphenylmethyl)piperazin-1-yl]ethyl}aminomethyl-5-methyl-1-phenylpyrazole [Compound 81]

Compound 81 was prepared was obtained using the same method as that of Example 1 except that 4-diphenylmethylpiperazin-1-ylethylamine and 5-methyl-1-phenyl pyrazole-3-carbaldehyde were used.

Yield: 71%

$^1$H NMR (300 MHz, CDCl$_3$) δ 7.33-7.46 (m, 8H), 7.12-7.32 (m, 7H), 6.27 (s, 1H), 4.22 (s, 1H), 3.98 (s, 2H), 2.93 (t, J=6.0 Hz, 2H), 2.64 (t, J=6.0 Hz, 2H), 2.50 (m, 4H), 2.38 (m, 4H), 2.29 (s, 3H)

$^{13}$C NMR (75 MHz, CDCl$_3$) δ 148.6, 142.7, 140.1, 139.5, 129.0, 128.4, 127.8, 127.7, 126.9, 124.8, 106.4, 76.1, 56.0, 53.2, 51.6, 45.9, 44.6, 12.3

IR (KBr, cm$^{-1}$) 3356 (—NH), 2924, 2810, 1502, 1452, 1008

FABHRMS m/z C$_{30}$H$_{36}$N$_5$ (M+H)$^+$ calculated value: 466.2971, measured value: 466.2983

EXAMPLE 82

Synthesis of 1-t-butyl-3-{2-[4-(4-diphenylmethyl)piperazin-1-yl]ethyl}aminomethyl-5-propyl pyrazole [Compound 82]

Compound 82 was prepared using the same method as that of Example 1 except that 4-diphenylmethylpiperazin-1-ylethylamine and 5-propyl-1-t-butylpyrazole-3-carbaldehyde were used.

Yield: 70%

$^1$H NMR (300 MHz, CDCl$_3$) δ 7.42 (d, J=7.1 Hz, 4H), 7.28 (t, J=7.3 Hz, 4H), 7.18 (t, J=7.3 Hz, 2H), 6.01 (s, 1H), 4.23 (s, 1H), 3.91 (s, 2H), 2.76 (t, J=6.0 Hz, 2H), 2.36-2.59 (m, 12H), 1.52-1.68 (m, 11H), 0.95 (t, J=7.4 Hz, 3H)

$^{13}$C NMR (75 MHz, CDCl$_3$) δ 149.9, 142.7, 141.6, 128.4, 127.9, 126.9, 105.5, 59.5, 57.7, 53.5, 51.9, 46.7, 46.0, 30.3, 23.0, 14.0

MP=81-81° C.

EXAMPLE 83

Synthesis of 3-{2-[4-(4-diphenylmethyl)piperazin-1-yl]ethyl}aminomethyl-1-phenyl-5-propylpyrazole [Compound 83]

Compound 83 was prepared using the same method as that of Example 1 except that 4-diphenylmethylpiperazin-1-ylethylamine and 5-propyl-1-phenylpyrazole-3-carbaldehyde were used.

Yield: 69%

$^1$H NMR (300 MHz, CDCl$_3$) δ 7.30-7.47 (m, 8H), 7.22-7.29 (m, 4H), 7.12-7.21 (m, 3H), 6.29 (s, 1H), 4.15 (s, 1H), 4.02(s, 2H), 2.96 (t, J=5.7 Hz, 2H), 2.66 (t, J=5.7 Hz, 2H), 2.25-2.62 (m, 8H), 2.37 (m, 2H), 1.59 (m, 2H), 0.89 (t, J=7.3 Hz, 3H)

$^{13}$C NMR (75 MHz, CDCl$_3$) δ 147.9, 145.2, 144.5, 142.6, 139.5, 129.0, 128.9, 128.4, 128.0, 127.8, 126.9, 125.3, 104.9, 76.1, 55.6, 53.1, 51.6, 28.2, 22.0, 13.7

IR (KBr, cm$^{-1}$) 3356 (—NH), 2958, 2810, 1500, 1452, 1010

FABHRMS m/z C$_{32}$H$_{40}$N$_5$ (M+H)$^+$ Calculated Value: 494.3284, Measured Value: 494.3305

EXAMPLE 84

Synthesis of 1-t-butyl-5-iso-butyl-3-{2-[4-(4-diphenylmethyl)piperazin-1-yl]ethyl}aminomethylpyrazole [Compound 84]

Compound 84 was prepared using the same method as that of Example 1 except that 4-diphenylmethylpiperazin-1-yl-ethylamine and 1-t-butyl-5-iso-butylpyrazole-3-carbaldehyde were used.

Yield: 82%

$^1$H NMR (300 MHz, CDCl$_3$) δ 7.43 (d, J=7.3 Hz, 4H), 7.28 (t, J=7.3 Hz, 4H), 7.18 (t, J=7.3 Hz, 2H), 5.99 (s, 1H), 4.23 (s, 1H), 3.92 (s, 2H), 2.76 (t, J=5.8 Hz, 2H), 2.44-2.57 (m, 12H), 1.86 (m, 1H), 1.61 (s, 9H), 0.92 (d, J=6.6 Hz, 6H)

$^{13}$C NMR (75 MHz, CDCl$_3$) δ 149.0, 142.7, 141.4, 128.4, 127.9, 126.9, 106.2, 76.2, 59.4, 57.7, 53.5, 51.8, 46.6, 46.0, 37.4, 30.3, 28.8, 22.5

MP=64-65° C.

EXAMPLE 85

Synthesis of 5-iso-butyl-3-{2-[4-(4-diphenylmethyl)piperazin-1-yl]ethyl}aminomethyl-1-phenylpyrazole [Compound 85]

Compound 85 was prepared using the same method as that of Example 1 except that 4-diphenylmethylpiperazin-1-yl-ethylamine and 5-iso-butyl-1-phenylpyrazole-3-carbaldehyde were used.

Yield: 86%

$^1$H NMR (300 MHz, CDCl$_3$) δ 7.35-7.47 (m, 8H), 7.23-7.32 (m, 5H), 7.12-7.23 (m, 2H), 6.27 (s, 1H), 4.16 (s, 1H), 4.01 (s, 2H), 2.93 (t, J=5.8 Hz, 2H), 2.64 (t, J=5.9 Hz, 4H), 2.37-2.56 (m, 6H), 2.37 (m, 2H), 1.79 (m, 1H), 0.84 (d, J=6.5 Hz, 6H)

$^{13}$C NMR (75 MHz, CDCl$_3$) δ 148.4, 144.3, 142.6, 139.6, 129.0, 128.9, 128.4, 128.0, 127.8, 126.8, 125.6, 105.4, 76.1, 55.9, 53.1, 51.6, 45.8, 44.5, 35.0, 29.6, 28.3, 22.3

IR (KBr, cm$^{-1}$) 3386 (—NH), 2956, 2810, 1502, 1452, 1008

FABHRMS m/z C$_{33}$H$_{42}$N$_5$ (M+H)$^+$ Calculated value: 508.3440, Measured value: 508.3413

EXAMPLE 86

Synthesis of 3-{2-[4-(4-diphenylmethyl)piperazin-1-yl]ethyl}aminomethyl-5-(2-furyl)-1-phenylpyrazole [Compound 86]

Compound 86 was prepared using the same method as that of Example 1 except that 4-diphenylmethylpiperazin-1-yl-ethylamine and 1-phenyl-5-(2-furyl)pyrazole-3-carbaldehyde were used.

Yield: 48%

$^1$H NMR (300 MHz, CDCl$_3$) δ 7.32-7.50 (m, 10H), 7.22-7.31 (m, 5H), 7.19 (s, 1H) 6.67 (m, 1H), 6.32 (m, 1H), 5.94 (m, 1H), 4.18 (s, 2H), 3.99 (s, 2H), 2.90 (m, 2H), 2.26-2.70 (m, 10H)

EXAMPLE 87

Synthesis of 1,5-diphenyl-3-{2-[4-(4-diphenyl methyl)piperazin-1-yl]ethyl}aminomethylpyrazole [Compound 87]

Compound 87 was prepared using the same method as that of Example 1 except that 4-diphenylmethylpiperazin-1-yl-ethylamine and 1,5-diphenylpyrazole-3-carbaldehyde were used.

Yield: 74%

$^1$H NMR (300 MHz, CDCl$_3$) δ 7.36-7.39 (m, 4H), 7.22-7.35 (m, 12H), 7.14-7.21 (m, 4H), 6.53 (s, 1H), 4.19 (s, 1H), 4.00 (s, 2H), 2.91 (t, J=6.0 Hz, 2H), 2.62 (t, J=6.0 Hz, 2H), 2.51 (m, 4H), 2.41 (m, 4H)

EXAMPLE 88

Synthesis of 1-t-butyl-3-{2-[4-(4-diphenylmethyl)piperazin-1-yl]ethyl}aminomethyl-5-(4-methylphenyl)pyrazole [Compound 88]

Compound 88 was prepared using the same method as that of Example 1 except that 4-diphenylmethylpiperazin-1-yl-ethylamine and 1-t-butyl-5-(4-methylphenyl)pyrazole-3-carbaldehyde were used.

Yield: 27%

$^1$H NMR (300 MHz, CDCl$_3$) δ 7.35-7.48 (m, 4H), 7.20-7.34 (m, 4H), 7.06-7.20 (m, 6H), 6.10 (s, 1H), 4.20 (s, 1H), 3.96 (s, 2H), 2.98 (m, 2H), 2.66 (m, 4H), 2.45-2.59 (m, 6H), 2.41 (s, 3H), 1.40 (s, 9H)

EXAMPLE 89

Synthesis of 1-t-butyl-5-(4-chlorophenyl)-3-{2-[4-(4-diphenylmethyl)piperazin-1-yl]ethyl}aminomethylpyrazole [Compound 89]

Compound 89 was prepared using the same method as that of Example 1 except that 4-diphenylmethylpiperazin-1-yl-ethylamine and 5-(4-chlorophenyl)-1-t-butylpyrazole-3-carbaldehyde were used.

Yield: 74%

$^1$H NMR (300 MHz, CDCl$_3$) δ 7.36-7.46 (m, 4H), 7.22-7.35 (m, 7H), 7.13-7.21 (m, 3H), 6.17 (s, 1H), 4.19 (s, 1H), 3.97 (s, 2H), 2.96 (t, J=5.8 Hz, 2H), 2.66 (t, J=5.8 Hz, 2H), 2.28-2.57 (m, 8H), 1.40 (s, 9H)

$^{13}$C NMR (75 MHz, CDCl$_3$) δ 144.4, 142.6, 134.6, 132.2, 131.5, 128.4, 128.0, 127.8, 126.9, 108.8, 61.3, 55.5, 53.1, 51.7, 45.6, 44.2, 31.1

IR (KBr, cm$^{-1}$) 3315 (—NH), 2932, 2812, 1450, 1092, 1008, 910

FABHRMS m/z C$_{33}$H$_{41}$ClN$_5$ (M+H)$^+$ calculated value: 542.3047, measured value: 542.3050

EXAMPLE 90

Synthesis of 5-(4-cyclohexylphenyl)-3-{2-[4-(4-diphenylmethyl)piperazin-1-yl]ethyl}aminomethyl-1-phenylpyrazole [Compound 90]

Compound 90 was prepared using the same method as that of Example 1 except that 4-diphenylmethylpiperazin-1-yl-ethylamine and 5-(4-cyclohexyl phenyl)-1-phenylpyrazole-3-carbaldehyde were used.

Yield: 72%

$^1$H NMR (300 MHz, CDCl$_3$) δ 7.40 (t, J=8.0 Hz, 4H), 7.20-7.30 (m, 9H), 7.18 (d, J=7.1 Hz, 2H), 7.04 (d, J=8.7 Hz,

2H), 6.79 (d, J=8.7 Hz, 2H), 6.46 (s, 1H), 4.25 (s, 1H), 4.04 (s, 2H), 2.66 (t, J=5.9 Hz, 2H), 2.33-2.62 (m, 11H), 1.68 (m, 4H), 1.44-1.63 (m, 6H)

EXAMPLE 91

Synthesis of 3-{2-[4-(4-diphenylmethyl)piperazin-1-yl]ethyl}aminomethyl-1-phenyl-5-(4-piperidin-1-yl) phenylpyrazole [Compound 91]

Compound 91 was prepared using the same method as that of Example 1 except that 4-diphenylmethylpiperazin-1-yl-ethylamine and 1-phenyl-5-(4-(piperidin-1-yl)phenyl)pyrazole-3-carbaldehyde were used.
Yield: 83%
$^1$H NMR (300 MHz, CDCl$_3$) δ 7.39 (d, J=7.2 Hz, 4H), 7.22-7.35 (m, 8H), 7.19 (d, J=7.1 Hz, 2H), 7.06-7.14 (m, 5H), 6.50 (s, 1H), 4.18 (s, 1H), 4.01 (s, 2H), 2.93 (t, J=5.6 Hz, 2H), 2.63 (t, J=5.6 Hz, 2H), 2.31-2.59 (m, 8H), 1.71-1.93 (m, 6H), 1.39 (t, J=9.7 Hz, 4H)

EXAMPLE 92

Synthesis of 3-{2-[4-(4-chlorobenzhydryl)piperazin-1-yl]ethyl}aminomethyl-5-methyl-1-phenylpyrazole [Compound 92]

Compound 92 was prepared using the same method as that of Example 1 except that 4-(4-chlorobenzhydryl)piperazin-1-ylethylamine and 5-methyl-1-phenylpyrazole-3-carbaldehyde were used.
Yield: 58%
$^1$H NMR (300 MHz, CDCl$_3$) δ 7.71 (m, 1H), 7.54 (m, 1H), 7.41 (d, J=7.4 Hz, 2H), 7.30-7.49 (m, 6H), 7.26 (d, J=6.7 Hz, 2H), 7.21 (d, J=8.8 Hz, 1H), 6.27 (s, 1H), 4.12 (s, 1H), 4.04 (s, 2H), 2.71-2.93 (m, 6H), 2.67 (t, J=5.6 Hz, 2H), 2.49 (m, 4H), 2.30 (s, 3H),
$^{13}$C NMR (75 MHz, CDCl$_3$) δ 167.7, 142.1, 141.2, 140.4, 139.4, 132.4, 130.9, 129.1, 129.0, 128.8, 128.7, 128.6, 127.7, 127.2, 124.8, 106.5, 75.4, 55.2, 53.0, 51.5, 45.4, 44.2, 12.3

EXAMPLE 93

Synthesis of 1-t-butyl-3-{2-[4-(4-chlorobenzhydryl)piperazin-1-yl]ethyl}aminomethyl-5-propylpyrazole [Compound 93]

Compound 93 was prepared using the same method as that of Example 1 except that 4-(4-chlorobenzhydryl)piperazin-1-ylethylamine and 5-propyl-1-t-butylpyrazole-3-carbaldehyde were used.
Yield: 86%
$^1$H NMR (300 MHz, CDCl$_3$) δ 7.33-7.41 (m, 4H), 7.16-7.32 (m, 5H), 6.01 (s, 1H), 4.21 (s, 1H), 3.91 (s, 2H), 2.75 (t, J=5.9 Hz, 2H), 2.53 (t, J=7.6 Hz, 4H), 7.31-7.46 (m, 8H), 1.54-1.69 (m, 11H), 0.95 (t, J=7.3 Hz, 3H)
$^{13}$C NMR (75 MHz, CDCl$_3$) δ 149.9, 142.1, 141.6, 141.3, 132.5, 129.2, 128.6, 128.5, 127.8, 127.1, 105.5, 75.4, 59.5, 57.7, 53.5, 51.8, 46.7, 46.0, 30.4, 30.3, 23.0, 14.0

EXAMPLE 94

Synthesis of 3-{2-[4-(4-chlorobenzhydryl)piperazin-1-yl]ethyl}aminomethyl-1-phenyl-5-propylpyrazole [Compound 94]

Compound 94 was prepared using the same method as that of Example 1 except that 4-(4-chlorobenzhydryl)piperazin-1-ylethylamine and 5-propyl-1-phenylpyrazole-3-carbaldehyde were used.
Yield: 95%
$^1$H NMR (300 MHz, CDCl$_3$) δ 7.30-7.45 (m, 8H), 7.13-7.29 (m, 6H), 6.26 (s, 1H), 4.14 (s, 1H), 3.99 (s, 2H), 2.92 (t, J=5.9 Hz, 2H), 2.63 (t, J=5.9 Hz, 2H), 2.56 (t, J=7.7 Hz, 2H), 2.47 (m, 4H), 2.35 (m, 2H), 1.47-1.66 (m, 2H), 0.90 (t, J=7.3 Hz, 3H)
$^{13}$C NMR (75 MHz, CDCl$_3$) δ 148.6, 145.1, 142.1, 141.3, 139.6, 132.5, 129.1, 129.0, 128.6, 128.5, 127.9, 127.7, 127.1, 125.3, 104.8, 75.4, 56.0, 53.1, 51.6, 46.0, 44.7, 28.2, 22.0, 13.7
IR (KBr, cm$^{-1}$) 3376 (—NH), 2958, 2928, 2812, 1502, 1010
FABHRMS m/z C$_{32}$H$_{39}$ClN$_5$ (M+H)$^+$ calculated value: 528.2894, measured value: 528.2895

EXAMPLE 95

Synthesis of 1-t-butyl-5-iso-butyl-3-{2-[4-(4-chlorobenzhydryl)piperazin-1-yl] ethyl}aminomethylpyrazole [Compound 95]

Compound 95 was prepared using the same method as that of Example 1 except that 4-(4-chlorobenzhydryl)piperazin-1-ylethylamine and 1-t-butyl-5-iso-butylpyrazole-3-carbaldehyde were used.
Yield: 68%
$^1$H NMR (300 MHz, CDCl$_3$) δ 7.37 (m, 4H), 7.16-7.34 (m, 5H), 5.98 (s, 1H), 4.21 (s, 1H), 3.91 (s, 2H), 2.75 (t, J=5.6 Hz, 2H), 2.53 (t, J=5.6 Hz, 2H), 2.30-2.49 (m, 10H), 1.85 (m, 1H), 1.61 (s, 9H), 0.91 (d, J=6.5 Hz, 6H)
$^{13}$C NMR (75 MHz, CDCl$_3$) δ 149.0, 142.1, 141.4, 141.3, 132.5, 129.2, 128.6, 128.5, 127.8, 127.1, 106.2, 75.4, 59.5, 57.7, 53.4, 51.8, 46.6, 46.0, 37.5, 30.3, 28.8, 22.5

EXAMPLE 96

Synthesis of 5-iso-butyl-3-{2-[4-(4-chlorobenzhydryl)piperazin-1-yl]ethyl}aminomethyl-1-phenylpyrazole [Compound 96]

Compound 96 was prepared using the same method as that of Example 1 except that 4-(4-chlorobenzhydryl)piperazin-1-ylethylamine and 5-iso-butyl-1-phenylpyrazole-3-carbaldehyde were used.
Yield: 95%
$^1$H NMR (300 MHz, CDCl$_3$) δ 7.12-7.51 (m, 14H), 6.28 (s, 1H), 4.19 (s, 1H), 3.86 (s, 2H), 2.90 (m, 4H), 2.77 (m, 4H), 2.35-2.61 (m, 6H), 1.80 (m, 1H), 0.84 (d, J=5.1 Hz, 6H)
$^{13}$C NMR (75 MHz, CDCl$_3$) δ 149.1, 143.9, 141.6, 140.8, 139.8, 132.6, 128.9, 128.6, 128.6, 127.8, 127.6, 127.2, 125.6, 106.5, 74.9, 54.8, 53.0, 51.5, 50.2, 48.7, 35.1, 28.3, 22.3

EXAMPLE 97

Synthesis of 3-{2-[4-(4-chlorobenzhydryl)piperazin-1-yl]ethyl}aminomethyl-5-(2-furyl)-1-phenylpyrazole [Compound 97]

Compound 97 was prepared using the same method as that of Example 1 except that 4-(4-chlorobenzhydryl)piperazin-1-ylethylamine and 1-phenyl-5-(2-furyl)pyrazole-3-carbaldehyde were used.
Yield: 62%
$^1$H NMR (300 MHz, CDCl$_3$) δ 7.29-7.44 (m, 10H), 7.26 (d, J=7.9 Hz, 4H), 7.22 (s, 1H), 6.67 (t, J=7.8 Hz, 1H), 6.32 (m, 1H), 5.93 (m, 1H), 4.14 (s, 1H), 4.03 (s, 2H), 2.94 (t, J=5.7 Hz, 2H), 2.65 (t, J=6.0 Hz, 4H), 2.50 (m, 4H), 2.36 (m, 2H)

¹³C NMR (75 MHz, CDCl₃) δ 144.1, 142.6, 142.4, 142.1, 141.3, 139.9, 135.5, 135.0, 132.5, 129.1, 129.0, 129.0, 128.6, 128.6, 127.7, 127.1, 125.7, 125.6, 111.2, 109.0, 105.4, 56.0, 53.1, 51.5, 45.8, 44.6, 29.7

IR (KBr, cm⁻¹) 3276 (—NH), 2926, 2814, 1504, 1010, 910

FABHRMS m/z C₃₃H₃₅ClN₅O (M+H)⁺ Calculated Value: 552.2507, Measured Value: 552.2530

EXAMPLE 98

Synthesis of 3-{2-[4-(4-chlorobenzhydryl)piperazin-1-yl]ethyl}aminomethyl-1,5-diphenylpyrazole [Compound 98]

Compound 98 was prepared using the same method as that of Example 1 except that 4-(4-chlorobenzhydryl)piperazin-1-ylethylamine and 1,5-diphenylpyrazole-3-carbaldehyde were used.

Yield: 61%

¹H NMR (300 MHz, CDCl₃) δ 7.34-7.41 (m, 4H), 7.23-7.33 (m, 10H), 7.14-7.22 (m, 5H), 6.53 (s, 1H), 4.16 (s, 1H), 4.00 (s, 2H), 2.91 (t, J=5.6 Hz, 2H), 2.61 (t, J=5.6 Hz, 2H), 2.49 (m, 4H), 2.38 (m, 4H)

EXAMPLE 99

Synthesis of 1-t-butyl-3-{2-[4-(4-chlorobenzhydryl)piperazin-1-yl]-ethyl}aminomethyl-5-(4-methylphenyl)pyrazole [Compound 99]

Compound 99 was prepared using the same method as that of Example 1 except for using 4-(4-chlorobenzhydryl)piperazin-1-ylethylamine and 1-t-butyl-5-(4-methylphenyl)pyrazole-3-carbaldehyde.

Yield: 41%

¹H NMR (300 MHz, CDCl₃) δ 7.32-7.40 (m, 4H), 7.18-7.31 (m, 5H), 7.13 (d, J=5.8 Hz, 2H), 7.08 (d, J=6.3 Hz, 2H), 6.15 (s, 1H), 4.18 (s, 1H), 4.06 (s, 2H), 2.72 (t, J=5.6 Hz, 4H), 2.49 (m, 4H), 2.32-2.45 (m, 7H), 1.38 (s, 9H)

¹³C NMR (75 MHz, CDCl₃) δ 141.9, 141.1, 138.5, 132.6, 130.4, 130.1, 129.1, 128.7, 128.6, 128.5, 128.4, 127.7, 127.2, 108.8, 61.5, 52.8, 51.6, 45.0, 43.5, 31.1, 31.1, 29.7, 21.3

IR (KBr, cm⁻¹) 3356 (—NH), 2924, 2814, 1450, 1010, 912, 806

FABHRMS m/z C₃₄H₄₄ClN₅(M+H)⁺ Calculated Value: 556.3207, Measured Value: 556.3207

EXAMPLE 100

Synthesis of 1-t-butyl-3-{2-[4-(4-chlorobenzhydryl)piperazin-1-yl]ethyl}aminomethyl-5-(4-chlorophenyl)pyrazole [Compound 100]

Compound 100 was prepared using the same method as that of Example 1 except that 4-(4-chlorobenzhydryl)piperazin-1-ylethylamine and 5-(4-chlorophenyl)-1-t-butyl pyrazole-3-carbaldehyde were used.

Yield: 57%

¹H NMR (300 MHz, CDCl₃) δ 7.30-7.41 (m, 6H), 7.08-7.29 (m, 8H), 6.22 (s, 1H), 4.18 (s, 1H), 4.05 (s, 2H), 3.03 (t, J=5.6 Hz, 2H), 2.72 (m, 4H), 2.30-2.59 (m, 6H), 1.39 (s, 9H)

¹³C NMR (75 MHz, CDCl₃) δ 142.8, 141.9, 141.1, 134.8, 132.6, 131.9, 131.5, 131.5, 129.1, 128.7, 128.6, 128.1, 128.0, 127.7, 127.2, 109.1, 61.5, 61.0, 54.5, 52.9, 51.6, 45.0, 43.5, 31.1, 29.7

IR (KBr, cm⁻¹) 3386 (—NH), 2928, 2816, 1488, 1092, 912

FABHRMS m/z C₃₃H₄₀ClN₅ (M+H)⁺ Calculated Value: 576.2657, Measured Value: 576.2661

EXAMPLE 101

Synthesis of 3-{2-[4-(4-chlorobenzhydryl)piperazin-1-yl]ethyl}aminomethyl-5-(4-cyclohexylphenyl)-1-phenylpyrazole [Compound 101]

Compound 101 was prepared using the same method as that of Example 1 except that 4-(4-chlorobenzhydryl)piperazin-1-ylethylamine and 5-(4-cyclohexyl phenyl)-1-phenyl pyrazole-3-carbaldehyde were used.

Yield: 31%

¹H NMR (300 MHz, CDCl₃) δ 7.31-7.39 (m, 6H), 7.11-7.30 (m, 8H), 7.06-7.16 (m, 3H), 7.04 (m, 1H), 6.50 (s, 1H), 4.13 (s, 1H), 4.05 (s, 2H), 2.99 (t, J=5.5 Hz, 2H), 2.66 (t, J=5.4 Hz, 4H), 2.41-2.69 (m, 6H), 2.36 (m, 1H), 1.70-1.94 (m, 6H), 1.39 (t, J=9.7 Hz, 4H)

EXAMPLE 102

Synthesis of 3-{2-[4-(4-chlorobenzhydryl)piperazin-1-yl]ethyl}aminomethyl-1-phenyl-5-(4-piperidine-1-ylphenyl)pyrazole [Compound 102]

Compound 102 was prepared using the same method as that of Example 1 except that 4-(4-chlorobenzhydryl)piperazin-1-ylethylamine and 1-phenyl-5-(4-piperidine-1-yl)phenyl)pyrazole-3-carbaldehyde were used.

Yield: 86.2%

¹H NMR (300 MHz, CDCl₃) δ 7.15-7.40 (m, 14H), 7.00 (m, 2H), 6.76 (m, 2H), 6.47 (s, 1H), 6.01 (brs, 1H), 4.24 (s, 1H), 4.11 (s, 2H), 2.56-2.77 (m, 6H), 2.49 (m, 6H), 2.32 (m, 2H), 1.51-1.74 (m, 6H)

¹³C NMR (75 MHz, CDCl₃) δ 176.2, 170.4, 151.6, 147.4, 144.8, 141.6, 139.9, 129.9, 129.3, 129.0, 129.0, 128.8, 128.7, 128.6, 128.6, 128.5, 127.7, 125.1, 115.2, 106.2, 74.9, 56.4, 54.7, 52.8, 51.5, 50.6, 49.5, 25.6, 24.2

EXAMPLE 103

Synthesis of 3-{2-[4-(2,3-dimethylphenyl)piperazin-1-yl]propyl}aminomethyl-5-methyl-1-phenylpyrazole [Compound 103]

Compound 103 was prepared using the same method as that of Example 1 except that 4-(2,3-dimethylphenyl)piperazin-1-ylpropylamine and 5-methyl-1-phenylpyrazole-3-carbaldehyde were used.

Yield: 49.0%

¹H NMR (300 MHz, CDCl₃) δ7.36 (m, 5H), 6.97 (m, 1H), 6.88 (m, 2H), 6.55 (s, 1H), 4.14 (m, 2H), 3.24 (m, 2H), 2.70 (m, 10H), 2.27 (s, 3H), 2.23 (s, 3H), 2.11 (s, 3H), 2.02 (m, 2H)

EXAMPLE 104

Synthesis of 3-{2-[4-(2,3-dimethylphenyl)piperazin-1-yl]propyl}aminomethyl-1,5-diphenylpyrazole [Compound 104]

Compound 104 was prepared using the same method as that of Example 1 except that 4-(2,3-dimethylphenyl)piperazin-1-ylpropylamine and 1,5-diphenylpyrazole-3-carbaldehyde were used.

Yield: 43.6%

¹H NMR (300 MHz, CDCl₃) δ 7.56 (d, J=7.7 Hz, 2H), 7.45 (t, J=7.5 Hz, 2H), 7.35 (t, J=7.0 Hz, 1H), 7.08 (t, J=7.6 Hz,

1H), 6.92 (m, 2H), 6.22 (s, 1H), 3.81 (m, 2H), 2.91 (m, 4H), 2.66 (m, 8H), 2.46 (t, J=6.9 Hz, 2H), 2.27 (s, 3H), 2.22 (s, 3H), 1.69 (m, 4H), 0.96 (t, J=8.3 Hz, 3H)

EXAMPLE 105

Synthesis of 3-{2-[4-(4-diphenylmethyl)piperazin-1-yl]propyl}aminomethyl-5-methyl-1-phenylpyrazole [Compound 105]

Compound 105 was prepared using the same method as that of Example 1 except that 4-diphenylmethylpiperazin-1-ylpropylamine and 5-methyl-1-phenylpyrazole-3-carbaldehyde were used.

Yield: 55.9%

$^1$H NMR (300 MHz, CDCl$_3$) δ 7.36 (m, 6H), 7.28 (m, 2H), 7.21 (m, 4H), 7.15 (m, 3H), 6.44 (s, 1H), 4.06 (s, 2H), 3.95 (s, 2H), 3.13 (m, 2H), 2.54 (m, 4H), 2.31 (m, 4H), 2.02 (m, 2H), 1.93 (m, 2H), 1.24 (s, 3H)

EXAMPLE 106

Synthesis of 3-{2-[4-(4-diphenylmethyl)piperazin-1-yl]propyl}aminomethyl-1,5-diphenylpyrazole [compound 106]

Compound 106 was prepared using the same method as that of Example 1 except that 4-diphenylmethylpiperazin-1-ylpropylamine and 1,5-diphenylpyrazole-3-carbaldehyde were used.

Yield: 53.2%

$^1$H NMR (300 MHz, CDCl$_3$) δ 7.51 (m, 2H), 7.41 (m, 6H), 7.26 (m, 4H), 7.18 (m, 3H), 6.19 (s, 1H), 4.20 (s, 1H), 3.78 (s, 2H), 2.65 (m, 4H), 2.39 (m, 8H), 2.05 (m, 2H), 1.71 (m, 4H), 1.01 (m, 3H)

EXAMPLE 107

Synthesis of 3-{2-[4-(2,3-dimethylphenyl)piperazin-1-yl]ethyl}methylaminomethyl-5-methyl-1-phenylpyrazole [Compound 107]

3-2-[4-(2,3-dimethyl phenyl)piperazin-1-yl]ethylaminomethyl-5-methyl-1-phenylpyrazole (30 mg, 0.074 mmol) and formaldehyde (0.06 ml, 0.743 mmol) were dissolved in 5 ml of purified CH$_2$Cl$_2$ and stirred at room temperature for 1 hour. NaBH(OAc)$_3$ (47.24 mg, 0.223 mmol) was added thereto and stirred for 6 hours at room temperature. The reaction progress and the completion were confirmed using TLC (CH$_2$Cl$_2$:MeOH=5:1). Upon completion of the reaction, water was added to the reaction mixture and the aqueous layer was extracted with CH$_2$Cl$_2$. The organic layer was dried over anhydrous MgSO$_4$, filtered and then concentrated under reduced pressure. The concentrate was separated by column chromatography (CH$_2$Cl$_2$:MeOH=10:1) to obtain the titled compound.

Yield: 77.4%

$^1$H NMR (300 MHz, CDCl$_3$) δ 7.44 (m, 5H), 7.06 (m, 1H), 6.91 (m, 2H), 6.27 (s, 1H), 3.75 (m, 2H), 2.93 (m, 6H), 2.75 (m, 6H), 2.45 (s, 3H), 2.33 (s, 3H), 2.26 (s, 3H), 2.21 (s, 3H)

EXAMPLE 108

Synthesis of 3-{2-[4-(2,3-dimethylphenyl)piperazin-1-yl]ethyl}methylaminomethyl-1-phenyl-5-propylpyrazole [Compound 108]

Compound 108 was prepared from 3-2-[4-(2,3-dimethylphenyl)piperazin-1-yl]ethylaminomethyl-1-phenyl-5-propylpyrazole using the same method as that of Example 107.

Yield: 87.2%

$^1$H NMR (300 MHz, CDCl$_3$) δ 7.65 (d, J=7.4 Hz, 2H), 7.45 (t, J=7.2 Hz, 2H), 7.35 (m, 1H), 7.08 (t, J=7.5 Hz, 1H), 6.91 (d, J=7.9 Hz, 2H), 6.20 (s, 1H), 3.53 (s, 2H), 2.91 (m, 4H), 2.59 (m, 10H), 2.28 (s, 6H), 2.19 (s, 3H), 1.73 (m, 2H), 1.00 (m, 3H)

EXAMPLE 109

Synthesis of 3-{2-[4-(2,3-dimethyl phenyl)piperazin-1-yl]ethyl}ethylaminoethyl-5-methyl-1-phenylpyrazole [Compound 109]

3-{2-[4-(2,3-dimethylphenyl)piperazin-1-yl]ethyl}aminoethyl-5-methyl-1-phenylpyrazole (30 mg, 0.074 mmol) and acetaldehyde (0.04 ml, 0.743 mmol) were dissolved in 5 ml of purified CH$_2$Cl$_2$ and stirred for 1 hour at room temperature. NaBH(OAc)$_3$ (47.24 mg, 0.223 mmol) was added thereto and stirred for 10 hours at room temperature. The reaction progress and completion was confirmed using TLC (CH$_2$Cl$_2$:MeOH=5:1). Upon completion of the reaction, water was added to the reaction mixture and the aqueous layer was extracted with CH$_2$Cl$_2$. The organic layer was dried over anhydrous MgSO$_4$, filtered and then was concentrated under reduced pressure. The concentrated solution was separated using column chromatography (CH$_2$Cl$_2$:MeOH=10:1) to obtain the titled compound.

Yield: 87.3%

$^1$H NMR (300 MHz, CDCl$_3$) δ 7.44 (m, 5H), 7.07 (m, 1H), 6.91 (m, 2H), 6.33 (s, 1H), 3.92 (s, 2H), 2.93 (m, 6H), 2.82 (m, 4H), 2.73 (m, 4H), 2.34 (s, 3H), 2.27 (s, 3H), 2.21 (s, 3H), 1.23 (t, J=8.5 Hz, 3H)

EXAMPLE 110

Synthesis of 3-{2-[4-(2,3-dimethylphenyl)piperazin-1-yl]ethyl}ethylaminoethyl-1-phenyl-5-propylpyrazole [Compound 110]

Compound 110 was prepared from 3-{2-[4-(2,3-dimethylphenyl)piperazin-1-yl]ethyl}aminoethyl-1-phenyl-5-propylpyrazole using the same method as that of Example 109.

Yield: 84.5%

$^1$H NMR (300 MHz, CDCl$_3$) δ 7.63 (d, J=7.2 Hz, 2H), 7.44 (t, J=7.8 Hz, 2H), 7.35 (m, 1H), 7.07 (t, J=7.3 Hz, 1H), 6.90 (d, J=7.6 Hz, 2H), 6.21 (s, 1H), 3.62 (s, 2H), 2.89 (m, 4H), 2.66 (m, 4H), 2.59 (m, 4H), 2.45 (m, 2H), 2.27 (s, 3H), 2.21 (s, 3H), 1.72 (m, 4H), 0.89 (m, 6H)

EXAMPLE 111

Synthesis of 3-{2-[4-(2,3-dimethylphenyl)piperazin-1-yl]propyl}ethylaminoethyl-1-phenyl-5-propylpyrazole [Compound 111]

Compound 111 was prepared from 3-{2-[4-(2,3-dimethylphenyl)piperazin-1-yl]propyl}aminoethyl-1-phenyl-5- propylpyrazole using the same method as that of Example 109.

Yield: 60.9%

$^1$H NMR (300 MHz, CDCl$_3$) δ 7.45 (m, 5H), 7.07 (t, J=7.7 Hz, 1H), 6.89 (m, 2H), 6.46 (s, 1H), 4.08 (s, 2H), 2.98 (m, 4H), 2.87 (m, 4H), 2.68 (m, 4H), 2.58 (m, 2H), 2.34 (s, 3H), 2.27 (s, 3H), 2.19 (s, 3H), 1.37 (m, 2H), 0.89 (m, 3H)

The following Table 2 summarizes the substituents according to Example 1 to Example 111 and the corresponding reaction scheme.

TABLE 2

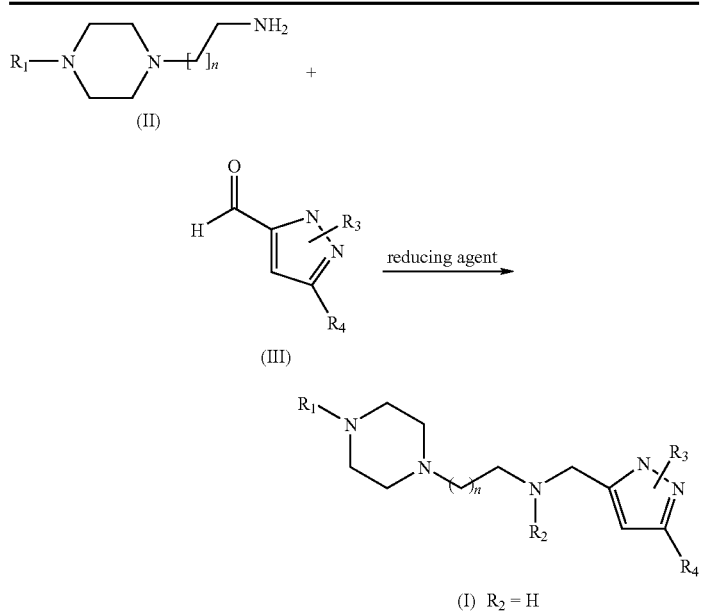

(I) R$_2$ = H

| Example | n | R1 | R2 | R3 | R4 |
|---|---|---|---|---|---|
| 1 | 1 | phenyl | hydrogen | hydrogen | methyl |
| 2 | 1 | phenyl | hydrogen | 1-phenyl | methyl |
| 3 | 1 | phenyl | hydrogen | 1-t-butyl | propyl |
| 4 | 1 | phenyl | hydrogen | 1-phenyl | propyl |
| 5 | 1 | phenyl | hydrogen | 1-t-butyl | iso-butyl |
| 6 | 1 | phenyl | hydrogen | 2-t-butyl | iso-butyl |
| 7 | 1 | phenyl | hydrogen | 2-t-butyl | iso-butyl |
| 8 | 1 | phenyl | hydrogen | 1-phenyl | 2-furyl |
| 9 | 1 | phenyl | hydrogen | 1-phenyl | phenyl |
| 10 | 1 | phenyl | hydrogen | 1-t-butyl | 4-methylphenyl |
| 11 | 1 | phenyl | hydrogen | 1-t-butyl | 4-chlorophenyl |
| 12 | 1 | phenyl | hydrogen | 1-phenyl | 4-cyclohexylphenyl |
| 13 | 1 | phenyl | hydrogen | 1-phenyl | 4-(piperidine-1-yl)phenyl |
| 14 | 1 | 2,3-dimethylphenyl | hydrogen | 1-phenyl | methyl |
| 15 | 1 | 2,3-dimethylphenyl | hydrogen | 1-t-butyl | propyl |
| 16 | 1 | 2,3-dimethylphenyl | hydrogen | 1-phenyl | propyl |
| 17 | 1 | 2,3-dimethylphenyl | hydrogen | 1-t-butyl | iso-butyl |
| 18 | 1 | 2,3-dimethylphenyl | hydrogen | 1-phenyl | iso-butyl |
| 19 | 1 | 2,3-dimethylphenyl | hydrogen | 1-phenyl | 2-furyl |
| 20 | 1 | 2,3-dimethylphenyl | hydrogen | 1-phenyl | phenyl |
| 21 | 1 | 2,3-dimethylphenyl | hydrogen | 1-t-butyl | 4-methylphenyl |
| 22 | 1 | 2,3-dimethylphenyl | hydrogen | 1-t-butyl | 4-chlorophenyl |
| 23 | 1 | 2,3-dimethylphenyl | hydrogen | 1-phenyl | 4-cyclohexylphenyl |
| 24 | 1 | 2,3-dimethylphenyl | hydrogen | 1-phenyl | 4-(piperidine-1-yl)phenyl |
| 25 | 1 | 2,3-dimethylphenyl | hydrogen | 1-phenyl | methyl |
| 26 | 1 | 2,3-dimethylphenyl | hydrogen | 1-t-butyl | propyl |
| 27 | 1 | 2,3-dimethylphenyl | hydrogen | 1-phenyl | propyl |
| 28 | 1 | 2,3-dimethylphenyl | hydrogen | 1-t-butyl | iso-butyl |
| 29 | 1 | 2,3-dimethylphenyl | hydrogen | 1-phenyl | iso-butyl |
| 30 | 1 | 2,3-dimethylphenyl | hydrogen | 1-phenyl | 2-furyl |
| 31 | 1 | 2,3-dimethylphenyl | hydrogen | 1-phenyl | phenyl |
| 32 | 1 | 2,3-dimethylphenyl | hydrogen | 1-t-butyl | 4-methylphenyl |
| 33 | 1 | 2,3-dimethylphenyl | hydrogen | 1-t-butyl | 4-chlorophenyl |
| 34 | 1 | 2,3-dimethylphenyl | hydrogen | 1-phenyl | 4-cyclohexylphenyl |
| 35 | 1 | 2,3-dimethylphenyl | hydrogen | 1-phenyl | 4-(piperidine-1-yl)phenyl |
| 36 | 1 | 4-methoxyphenyl | hydrogen | hydrogen | methyl |
| 37 | 1 | 4-methoxyphenyl | hydrogen | 1-phenyl | methyl |
| 38 | 1 | 4-methoxyphenyl | hydrogen | 1-t-butyl | propyl |

TABLE 2-continued

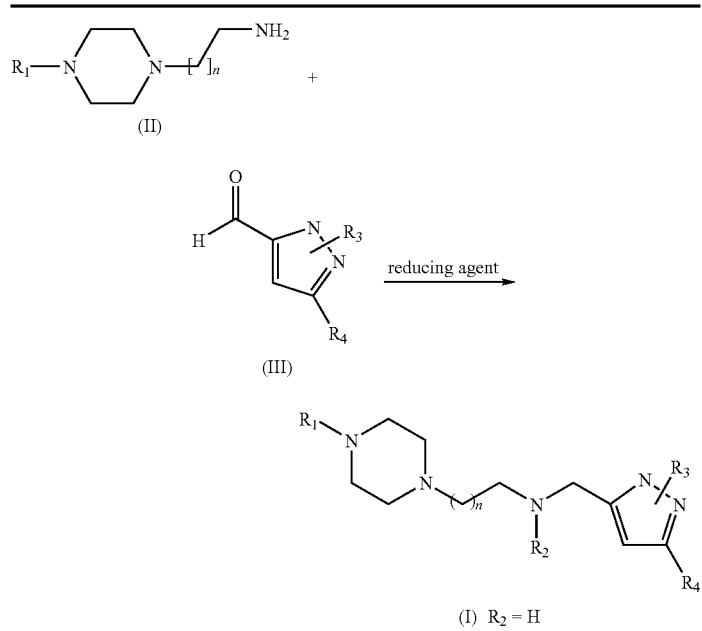

| Example | n | R1 | R2 | R3 | R4 |
|---|---|---|---|---|---|
| 39 | 1 | 4-methoxyphenyl | hydrogen | 1-phenyl | propyl |
| 40 | 1 | 4-methoxyphenyl | hydrogen | 1-t-butyl | iso-butyl |
| 41 | 1 | 4-methoxyphenyl | hydrogen | 2-t-butyl | iso-butyl |
| 42 | 1 | 4-methoxyphenyl | hydrogen | 1-phenyl | iso-butyl |
| 43 | 1 | 4-methoxyphenyl | hydrogen | 1-phenyl | 2-furyl |
| 44 | 1 | 4-methoxyphenyl | hydrogen | 1-phenyl | phenyl |
| 45 | 1 | 4-methoxyphenyl | hydrogen | 1-t-butyl | 4-methylphenyl |
| 46 | 1 | 4-methoxyphenyl | hydrogen | 1-t-butyl | 4-chlorophenyl |
| 47 | 1 | 4-methoxyphenyl | hydrogen | 1-phenyl | 4-cyclohexylphenyl |
| 48 | 1 | 4-methoxyphenyl | hydrogen | 1-phenyl | 4-(piperidine-1-yl)phenyl |
| 49 | 1 | 4-nitrophenyl | hydrogen | 1-phenyl | methyl |
| 50 | 1 | 4-nitrophenyl | hydrogen | 1-t-butyl | propyl |
| 51 | 1 | 4-nitrophenyl | hydrogen | 1~phenyl | propyl |
| 52 | 1 | 4-nitrophenyl | hydrogen | 1-t-butyl | iso-butyl |
| 53 | 1 | 4-nitrophenyl | hydrogen | 1-phenyl | iso-butyl |
| 54 | 1 | 4-nitrophenyl | hydrogen | 1-phenyl | 2-furyl |
| 55 | 1 | 4-nitrophenyl | hydrogen | 1-phenyl | phenyl |
| 56 | 1 | 4-nitrophenyl | hydrogen | 1-t-butyl | 4-methylphenyl |
| 57 | 1 | 4-nitrophenyl | hydrogen | 1-t-butyl | 4-chlorophenyl |
| 58 | 1 | 4-nitrophenyl | hydrogen | 1-phenyl | 4-cyclohexylphenyl |
| 59 | 1 | 4-nitrophenyl | hydrogen | 1-phenyl | 4-(piperidine-1-yl)phenyl |
| 60 | 1 | 2-flurophenyl | hydrogen | hydrogen | methyl |
| 61 | 1 | 2-flurophenyl | hydrogen | 1-phenyl | methyl |
| 62 | 1 | 2-flurophenyl | hydrogen | 1-t-butyl | propyl |
| 63 | 1 | 2-flurophenyl | hydrogen | 1-phenyl | propyl |
| 64 | 1 | 2-flurophenyl | hydrogen | 1-t-butyl | iso-butyl |
| 65 | 1 | 2-flurophenyl | hydrogen | 2-t-butyl | iso-butyl |
| 66 | 1 | 2-flurophenyl | hydrogen | 1-phenyl | iso-butyl |
| 67 | 1 | 2-flurophenyl | hydrogen | 1-phenyl | 2-furyl |
| 68 | 1 | 2-flurophenyl | hydrogen | 1-phenyl | phenyl |
| 69 | 1 | 2-flurophenyl | hydrogen | 1-t-butyl | 4-methylphenyl |
| 70 | 1 | 2-flurophenyl | hydrogen | 1-t-butyl | 4-chlorophenyl |
| 71 | 1 | 2-flurophenyl | hydrogen | 1-phenyl | 4-cyclohexylphenyl |
| 72 | 1 | 2-flurophenyl | hydrogen | 1-phenyl | 4-(piperidine-1-yl)phenyl |
| 73 | 1 | 3-chlorophenyl | hydrogen | hydrogen | methyl |
| 74 | 1 | 3-chlorophenyl | hydrogen | 1-phenyl | methyl |
| 75 | 1 | 3-chlorophenyl | hydrogen | 1-t-butyl | propyl |

TABLE 2-continued

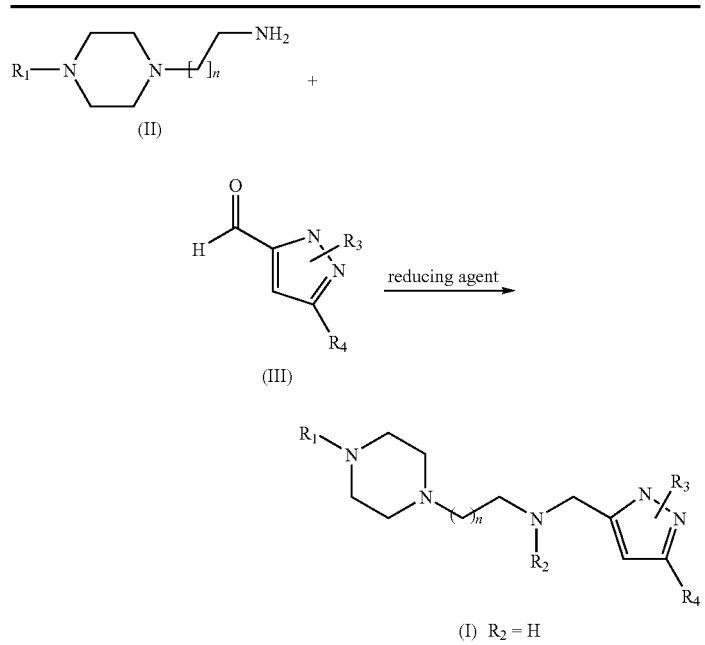

| Example | n | R1 | R2 | R3 | R4 |
|---|---|---|---|---|---|
| 76 | 1 | 3-chlorophenyl | hydrogen | 1-phenyl | propyl |
| 77 | 1 | 3-chlorophenyl | hydrogen | 1-t-butyl | iso-butyl |
| 78 | 1 | 3-chlorophenyl | hydrogen | 2-t-butyl | iso-butyl |
| 79 | 1 | 3-chlorophenyl | hydrogen | 1-phenyl | iso-butyl |
| 80 | 1 | 3-chlorophenyl | hydrogen | 1-phenyl | 2-furyl |
| 81 | 1 | diphenylmethyl | hydrogen | 1-phenyl | methyl |
| 82 | 1 | diphenylmethyl | hydrogen | 1-t-butyl | propyl |
| 83 | 1 | diphenylmethyl | hydrogen | 1-phenyl | propyl |
| 84 | 1 | diphenylmethyl | hydrogen | 1-t-butyl | iso-butyl |
| 85 | 1 | diphenylmethyl | hydrogen | 1-phenyl | iso-butyl |
| 86 | 1 | diphenylmethyl | hydrogen | 1-phenyl | 2-furyl |
| 87 | 1 | diphenylmethyl | hydrogen | 1-phenyl | phenyl |
| 88 | 1 | diphenylmethyl | hydrogen | 1-t-butyl | 4-methylphenyl |
| 89 | 1 | diphenylmethyl | hydrogen | 1-t-butyl | 4-chlorophenyl |
| 90 | 1 | diphenylmethyl | hydrogen | 1-phenyl | 4-cyclohexylphenyl |
| 91 | 1 | diphenylmethyl | hydrogen | 1-phenyl | 4-(piperidine-1-yl)phenyl |
| 92 | 1 | 4-chlorobenzhydril | hydrogen | 1-phenyl | methyl |
| 93 | 1 | 4-chlorobenzhydril | hydrogen | 1-t-butyl | propyl |
| 94 | 1 | 4-chlorobenzhydril | hydrogen | 1-phenyl | propyl |
| 95 | 1 | 4-chlorobenzhydril | hydrogen | 1-t-butyl | iso-butyl |
| 96 | 1 | 4-chlorobenzhydril | hydrogen | 1-phenyl | iso-butyl |
| 97 | 1 | 4-chlorobenzhydril | hydrogen | 1-phenyl | 2-furyl |
| 98 | 1 | 4-chlorobenzhydril | hydrogen | 1-phenyl | phenyl |
| 99 | 1 | 4-chlorobenzhydril | hydrogen | 1-t-butyl | 4-methylphenyl |
| 100 | 1 | 4-chlorobenzhydril | hydrogen | 1-t-butyl | 4-chlorophenyl |
| 101 | 1 | 4-chlorobenzhydril | hydrogen | 1-phenyl | 4-cyclohexylphenyl |
| 102 | 1 | 4-chlorobenzhydril | hydrogen | 1-phenyl | 4-(piperidine-1-yl)phenyl |
| 103 | 2 | 2,3-dimethylphenyl | hydrogen | 1-phenyl | methyl |
| 104 | 2 | 2,3-dimethylphenyl | hydrogen | 1-phenyl | phenyl |
| 105 | 2 | diphenylmethyl | hydrogen | 1-phenyl | methyl |
| 106 | 2 | diphenylmethyl | hydrogen | 1-phenyl | phenyl |

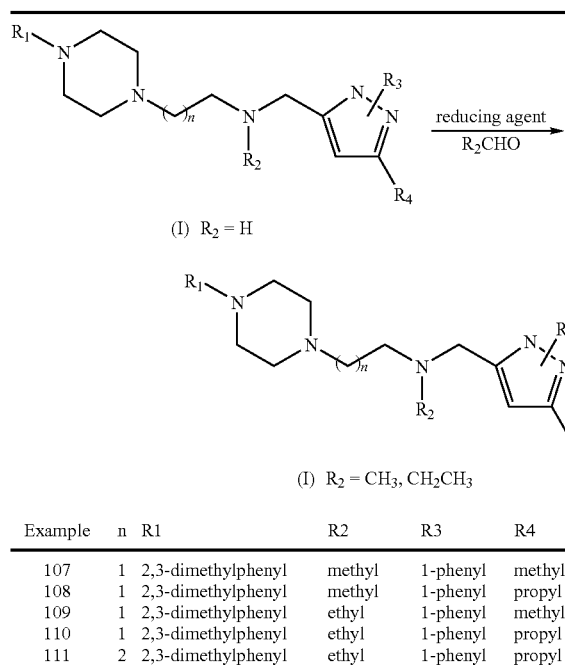

| Example | n | R1 | R2 | R3 | R4 |
|---------|---|----|----|----|----|
| 107 | 1 | 2,3-dimethylphenyl | methyl | 1-phenyl | methyl |
| 108 | 1 | 2,3-dimethylphenyl | methyl | 1-phenyl | propyl |
| 109 | 1 | 2,3-dimethylphenyl | ethyl | 1-phenyl | methyl |
| 110 | 1 | 2,3-dimethylphenyl | ethyl | 1-phenyl | propyl |
| 111 | 2 | 2,3-dimethylphenyl | ethyl | 1-phenyl | propyl |

Evaluation of Pharmacological Effects

In order to evaluate the pharmaceutical effects induced by the compounds of the present invention, the inhibitory effects were examined according to the following procedure. As the first step, those that show more than 50% of inhibition to the calcium channel ($\alpha_{1H}$) expressed in *Xenopus oocytes* were screened. For the second step, $\alpha_{1G}$ $Ca^{2+}$ channel activities expressed in HEK 293 cells were measured to determine the effective inhibition concentration $IC_{50}$.

Measurement of T-type $Ca^{2+}$ Channel Blocking Activity of HEK293 Cells by Using Electrophysiological Method The culture medium was prepared by adding 10% fetal bovine serum (FBS) and 1% penicillin/streptomycin (v/v) to Dulbecco's modified Eagle's medium (DMEM). The cells were cultured in an incubator having a wet condition of 95% air/5% $CO_2$ at 37° C. The medium was replaced every 3 to 4 days and the cells were sub-cultured every week such that only the cells that expressed $\alpha_{1G}$ T-type $Ca^{2+}$ channels could be grown using G-418 (0.5 mg/ml) solution. The cells that were used to measure T-type $Ca^{2+}$ channel activity were incubated on a cover slip coated by poly-L-lysine (0.5 mg/ml) every time they were sub-cultured and then recorded after 2 to 3 days. T-type $Ca^{2+}$ channel currents at the single-cell level were determined by the electrophysiological whole-cells patch clamp technique using EPC-9 amplifier (HEKA, German). Extracellular solution of NaCl 140 mM, $CaCl_2$ 2 mM, HEPES 10 mM (pH 7.4), and intracellular solution of KCl 130 mM, HEPES 10 mM, EGTA 11 mM, MgATP 5 mM (pH 7.4) were used for T-type $Ca^{2+}$ channel blocking activity. As the low voltage-activated T-type $Ca^{2+}$ channel activity protocol, a fine glass electrode of 3-4 MΩ resistance containing the above-prepared intracellular solution was inserted into a single cell to become the whole-cell recording mode, followed by fixing the potential of the cell membrane at −100 mV and measuring the inward current of the T-type $Ca^{2+}$ channel activity when hypopolarized at −30 mV (50 ms duration) every 15 seconds. Each compound was dissolved in 100% dimethylsulfoxide (DMSO) to prepare 10 mM stock solution, and then the effect of T-type $Ca^{2+}$ channel current at 1,000 fold diluted concentration of 10 μM (including 0.1% DMSO) was initially measured before $IC_{50}$ values were determined by testing the effects at the concentration range for the $IC_{50}$ measurement (in general, 0.1-100 μM). Specifically, cells were treated with each compound along with the extracellular solution until T-type $Ca^{2+}$ channel currents were stabilized under whole-cell voltage-clamp conditions and the inhibition level of the peak current due to the compound was calculated and expressed in percentage. From these results the effective inhibition concentration was determined, and the results thereof are shown in the following Table 3.

TABLE 3

| compound | % Inhibition in oocyte (100 μM) | % Inhibition in HEK293 (10 μM) | $IC_{50}$ (μM) |
|----------|------|------|------|
| compound 4 | 80.14 | 94.5 ± 2.8 | 0.30 ± 0.03 |
| compound 7 | 77.08 | 87.9 ± 2.7 | 0.82 ± 0.04 |
| compound 15 | 27.50 | 79.4 ± 1.6 | 1.43 ± 0.15 |
| compound 16 | 74.60 | 95.9 ± 0.7 | 0.58 ± 0.05 |
| compound 18 | 92.04 | 92.7 ± 5.7 | 1.02 ± 0.10 |
| compound 37 | — | 53.0 ± 1.6 | 9.41 ± 0.55 |
| compound 39 | 67.83 | 91.6 ± 0.5 | 0.90 ± 0.07 |
| compound 42 | 73.34 | 95.6 ± 1.8 | 1.04 ± 0.15 |
| compound 51 | 51.27 | 95.3 ± 1.4 | 0.66 ± 0.07 |
| compound 52 | 56.43 | 94/1 ± 0.5 | 1.77 ± 0.20 |
| compound 53 | 74.44 | 94.8 ± 1.3 | 1.06 ± 0.02 |
| compound 63 | 54.94 | 93.8 ± 1.4 | 0.66 ± 0.04 |
| compound 76 | 44.68 | 75.8 ± 1.0 | 0.90 ± 0.09 |
| compound 81 | 95.42 | 97.4 ± 1.3 | 0.57 ± 0.06 |
| compound 82 | 24.76 | 60.5 ± 0.6 | 4.42 ± 0.89 |
| compound 83 | 97.81 | 92.4 ± 1.8 | 0.30 ± 0.04 |
| compound 84 | 40.35 | 89.9 ± 0.3 | 2.19 ± 0.03 |
| compound 92 | 34.52 | 79.2 ± 3.3 | 0.33 ± 0.66 |
| compound 94 | 92.93 | 100 | 0.65 ± 0.03 |
| Mibefradil | 86.0 | — | 0.84 |

As shown in the above results of the experiments, the compounds of present invention as represented by Formula 1 has an inhibitory effect of T-type $Ca^{2+}$ channel, and particularly Compounds 4, 7, 16, 51, 63, 81, 83, 92, 94 were shown to have inhibitory effect of T-type $Ca^{2+}$ channel similar to or stronger than that of mibefradil.

The present invention provides novel compounds and the preparation method thereof. Since the compounds of the present invention can selectively block T-type $Ca^{2+}$ ion channels, they are much more effective in treating pain, high blood pressure and epilepsy than any other conventional drugs.

What is claimed is:

1. Piperazinylalkylpyrazole compounds represented by Formula I:

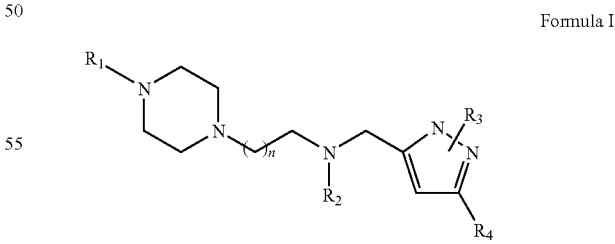

Formula I wherein,
 $R_1$ represents phenyl optionally substituted with from one to five of nitro, methyl, chloro, methoxy; 1,1-diphenyl methyl wherein the phenyl groups are optionally substituted with one to five of chloro or methyl; or phenyl substituted with 2-fluoro $R_2$ represents hydrogen, methyl or ethyl;

R₃ represents methyl, propyl, isobutyl, cyclohexyl, phenyl optionally substituted with one or more of methyl, chloro, or methoxy; naphthyl, or piperidinyl;

R₄ represents hydrogen, $C_{1-6}$ alkyl, 2-furyl, or phenyl optionally substituted with from one to five of chloro, methyl, cyclohexyl, or piperidinyl; and n represents an integer from 0 to 3; or a pharmaceutically acceptable salt thereof.

2. The compound of claim 1 selected from the group consisting of:

5-methyl-3-[2-(4-phenylpiperazin-1-yl)ethyl]aminomethylpyrazole;

5-methyl-1-phenyl-3-[2-(4-phenylpiperazin-1-yl)ethyl]aminomethylpyrazole;

1-t-butyl-5-propyl-3-[2-(4-phenylpiperazin-1-yl)ethyl]aminomethylpyrazole;

5-propyl-1-phenyl-3-[2-(4-phenylpiperazin-1-yl)ethyl]aminomethylpyrazole;

1-t-butyl-5-iso-butyl-3-[2-(4-phenylpiperazin-1-yl)ethyl]aminomethylpyrazole;

2-t-butyl-5-iso-butyl-3-[2-(4-phenylpiperazin-1-yl)ethyl]aminomethylpyrazole;

5-iso-butyl-1-phenyl-3-[2-(4-phenylpiperazin-1-yl)ethyl]aminomethylpyrazole;

5-(furan-2-yl)-1-phenyl-3-[2-(4-phenylpiperazin-1-yl)ethyl]aminomethylpyrazole;

1,5-diphenyl-3-[2-(4-phenylpiperazin-1-yl)ethyl]aminomethylpyrazole;

1-t-butyl-5-(4-methylphenyl)-3-[2-(4-phenylpiperazin-1-yl)ethyl]aminomethylpyrazole;

1-t-butyl-5-(4-chlorophenyl)-3-[2-(4-phenylpiperazin-1-yl)ethyl]aminomethylpyrazole;

5-(4-cyclohexyiphenyl)-1-phenyl-3-[2-(4-phenylpiperazin-1-yl)ethyl]aminomethylpyrazole;

1-phenyl-3-[2-(4-phenylpiperazin-1-yl)ethyl]aminomethyl-5-(4-piperidin-1-yl)phenylpyrazole;

3-{2-[4-(2,3-dimethylphenyl)piperazin-1-yl]ethyl}aminomethyl-5-methyl-1-phenylpyrazole;

1-t-butyl-3-{2-[4-(2,3-dimethylphenyl)piperazin-1-yl]ethyl}aminomethyl-5-propylpyrazole;

3-{2-[4-(2,3-dimethylphenyl)piperazin-1-yl]ethyl}aminomethyl-1-phenyl-5-propylpyrazole;

1-t-butyl-5-iso-butyl-3-{2-[4-(2,3-dimethylphenyl)piperazin-1-yl]ethyl}aminomethylpyrazole;

5-iso-butyl-3-{2-[4-(2,3-dimethylphenyl)piperazin-1-yl]ethyl}aminomethyl-1-phenylpyrazole;

3-{2-[4-(2,3-dimethylphenyl)piperazin-1-yl]ethyl}aminomethyl-5-(furan-2-yl)-1-phenylpyrazole;

3-{2-[4-(2,3-dimethylphenyl)piperazin-1-yl]ethyl}aminomethyl-1,5-diphenylpyrazole;

1-t-butyl-3-{2-[4-(2,3-dimethylphenyl)piperazin-1-yl]ethyl}aminomethyl-5-(4-methylphenyl)pyrazole;

1-t-butyl-3-{2-[4-(2,3-dimethylphenyl)piperazin-1-yl]ethyl}aminomethyl-5-(4-chlorophenyl)pyrazole;

5-(4-cyclohexylphenyl)-3-{2-[4-(2,3-dimethylphenyl)piperazin-1-yl]ethyl}aminomethyl-1-phenylpyrazole;

3-{2-[4-(2,3-dimethylphenyl)piperazin-1-yl]ethyl}aminomethyl-1-phenyl-5-(4-piperidin-1-yl)phenylpyrazole;

3-{2-[4-(2,4-dimethylphenyl)piperazin-1-yl]ethyl}aminomethyl-5-methyl-1-phenylpyrazole;

1-t-butyl-3-{2-[4-(2,4-dimethylphenyl)piperazin-1-yl]ethyl}aminomethyl-5-propylpyrazole;

3-{2-[4-(2,4-dimethylphenyl)piperazin-1-yl]ethyl}aminomethyl-1-phenyl-5-propylpyrazole;

1-t-butyl-5-iso-butyl-3-{2-[4-(2,4-dimethylphenyl)piperazin-1-yl]ethyl}aminomethylpyrazole;

5-iso-butyl-3-{2-[4-(2,4-dimethylphenyl)piperazin-1-yl]ethyl}aminomethyl-1-phenylpyrazole;

3-{2-[4-(2,4-dimethylphenyl)piperazin-1-yl]ethyl}aminomethyl-5-(furan-2-yl)-1-phenylpyrazole;

3-{2-[4-(2,4-dimethylphenyl)piperazin-1-yl]ethyl}aminomethyl-1,5-diphenylpyrazole;

1-t-butyl-3-{2-[4-(2,4-dimethylphenyl)piperazin-1-yl]ethyl}aminomethyl-5-(4-methyl)phenylpyrazole;

1-t-butyl-5-(4-chlorophenyl)-3-{2-[4-(2,4-dimethylphenyl)piperazin-1-yl]-ethyl}aminomethylpyrazole;

5-(4-cyclohexylphenyl)-3-{2-[4-(2,4-dimethylphenyl)piperazin-1-yl]ethyl}aminomethyl-1-phenylpyrazole;

3-{2-[4-(2,4-dimethylphenyl)piperazin-1-yl]ethyl}aminomethyl-1-phenyl-5-(4-piperidine-1-yl)phenylpyrazole;

3-{2-[4-(4-methoxyphenyl)piperazin-1-yl]ethyl}aminomethyl-5-methylpyrazole;

3-{2-[4-(4-methoxyphenyl)piperazin-1-yl]ethyl}aminomethyl-5-methyl-1-phenylpyrazole;

1-t-butyl-3-{2-[4-(4-methoxyphenyl)piperazin-1-yl]ethyl}aminomethyl-5-propylpyrazole;

3-{2-[4-(4-methoxyphenyl)piperazin-1-yl]ethyl}aminomethyl-5-propyl-1-phenylpyrazole;

1-t-butyl-5-iso-butyl-3-{2-[4-(4-methoxyphenyl)piperazin-1-yl]ethyl}aminomethylpyrazole;

2-t-butyl-5-iso-butyl-3-{2-[4-(4-methoxyphenyl)piperazin-1-yl]ethyl}aminomethylpyrazole;

5-iso-butyl-3-{2-[4-(4-methoxyphenyl)piperazin-1-yl]ethyl}aminomethyl-1-phenylpyrazole;

5-(furan-2-yl)-3-{2-[4-(4-methoxyphenyl)piperazin-1-yl]ethyl}aminomethyl-1-phenylpyrazole;

3-{2-[4-(4-methoxyphenyl)piperazin-1-yl]ethyl}aminomethyl-1,5-phenylpyrazole;

1-t-butyl-5-(4-methylphenyl)-3-{2-[4-(4-methoxyphenyl)piperazin-1-yl]ethyl}aminomethylpyrazole;

1-t-butyl-5-(4-chlorophenyl)-3-{2-[4-(4-methoxyphenyl)piperazin-1-yl]ethyl}aminomethylpyrazole;

5-(4-cyclohexylphenyl)-3-{2-[4-(4-methoxyphenyl)piperazin-1-yl]ethyl}aminomethyl-1-phenylpyrazole;

3-{2-[4-(4-methoxyphenyl)piperazin-1-yl]ethyl}aminomethyl-1-phenyl-5-(4-piperidine-1-yl)phenylpyrazole;

5-methyl-3-{2-[4-(4-nitrophenyl)piperazin-1-yl]ethyl}aminomethyl-1-phenylpyrazole;

1-t-butyl-3-{2-[4-(4-nitrophenyl)piperazin-1-yl]ethyl}aminomethyl-5-propylpyrazole;

3-{2-[4-(4-nitrophenyl)piperazin-1-yl]ethyl}aminomethyl-1-phenyl-5-propylpyrazole;

1-t-butyl-5-iso-butyl-3-{2-[4-(4-nitrophenyl)piperazin-1-yl]ethyl}aminomethylpyrazole;

5-iso-butyl-3-{2-[4-(4-nitrophenyl)piperazin-1-yl]ethyl}aminomethyl-1-phenylpyrazole;

5-(furan-2-yl)-3-{2-[4-(4-nitrophenyl)piperazin-1-yl]ethyl}aminomethyl-1-phenylpyrazole;

1,5-diphenyl-3-{2-[4-(4-nitrophenyl)piperazin-1-yl]ethyl}aminomethylpyrazole;

1-t-butyl-5-(4-methylphenyl)-3-{2-[4-(4-nitrophenyl)piperazin-1-yl]ethyl}aminomethylpyrazole;

1-t-butyl-5-(4-chlorophenyl)-3-{2-[4-(4-nitrophenyl)piperazin-1-yl]ethyl}aminomethylpyrazole;

5-(4-cyclohexylphenyl)-3-{2-[4-(4-nitrophenyl)piperazin-1-yl]ethyl}aminomethyl-1-phenylpyrazole;
1-phenyl-5-(4-piperidin-1-yl)phenyl-3-{2-[4-(4-nitrophenyl)piperazin-1-yl]ethyl}aminomethylpyrazole;
3-{2-[4-(2-fluorophenyl)piperazin-1-yl]ethyl}aminomethyl-5-methylpyrazole;
3-{2-[4-(2-fluorophenyl)piperazin-1-yl]ethyl}aminomethyl-5-methyl-1-phenylpyrazole;
1-t-butyl-3-{2-[4-(2-fluorophenyl)piperazin-1-yl]ethyl}aminomethyl-5-propylpyrazole;
3-{2-[4-(2-fluorophenyl)piperazin-1-yl]ethyl}aminomethyl-1-phenyl-5-propylpyrazole;
1-t-butyl-5-iso-butyl-3-{2-[4-(2-fluorophenyl)piperazin-1-yl]ethyl}aminomethylpyrazole;
2-t-butyl-5-iso-butyl-3-{2-[4-(2-fluorophenyl)piperazin-1-yl]ethyl}aminomethylpyrazole;
5-iso-butyl-3-{2-[4-(2-fluorophenyl)piperazin-1-yl]ethyl}aminomethyl-1-phenylpyrazole;
3-{2-[4-(2-fluorophenyl)piperazin-1-yl]ethyl}aminomethyl-5-(furan-2-yl)-1-phenylpyrazole;
1,5-diphenyl-3-{2-[4-(2-fluorophenyl)piperazin-1-yl]ethyl}aminomethylpyrazole;
1-t-butyl-3-{2-[4-(2-fluorophenyl)piperazin-1-yl]ethyl}aminomethyl-5-(4-methyl)phenylpyrazole;
1-t-butyl-5-(4-chlorophenyl)-3-{2-[4-(2-fluorophenyl)piperazin-1-yl]ethyl}aminomethylpyrazole;
5-(4-cyclohexylphenyl)-3-{2-[4-(2-fluorophenyl)piperazin-1-yl]ethyl}aminomethyl-1-phenylpyrazole;
3-{2-[4-(2-fluorophenyl)piperazin-1-yl]ethyl}aminomethyl-1-phenyl-5-(4-piperidine-1-yl)phenylpyrazole;
3-{2-[4-(3-chlorophenyl)piperazin-1-yl]ethyl}aminomethyl-5-methylpyrazole;
3-{2-[4-(3-chlorophenyl)piperazin-1-yl]ethyl}aminomethyl-5-methyl-1-phenylpyrazole;
1-t-butyl-3-{2-[4-(3-chlorophenyl)piperazin-1-yl]ethyl}aminomethyl-5-propylpyrazole;
3-{2-[4-(3-chlorophenyl)piperazin-1-yl]ethyl}aminomethyl-1-phenyl-5-propylpyrazole;
1-t-butyl-5-iso-butyl-3-{2-[4-(3-chlorophenyl)piperazin-1-yl]ethyl}aminomethylpyrazole;
2-t-butyl-5-iso-butyl-3-{2-[4-(3-chlorophenyl)piperazin-1-yl]ethyl}aminomethylpyrazole;
5-iso-butyl-3-{2-[4-(3-chlorophenyl)piperazin-1-yl]ethyl}aminomethyl-1-phenylpyrazole;
3-{2-[4-(3-chlorophenyl)piperazin-1-yl]ethyl}aminomethyl-5-(furan-2-yl)-1-phenylpyrazole;
3-{2-[4-(4-diphenylmethyl)piperazin-1-yl]ethyl}aminomethyl-5-methyl-1-phenylpyrazole;
1-t-butyl-3-{2-[4-(4-diphenylmethyl)piperazin-1-yl]ethyl}aminomethyl-5-propylpyrazole;
3-{2-[4-(4-diphenylmethyl)piperazin-1-yl]ethyl}aminomethyl-1-phenyl-5-propylpyrazole;
1-t-butyl-5-iso-butyl-3-{2-[4-(4-diphenylmethyl)piperazin-1-yl]ethyl}aminomethylpyrazole;
5-iso-butyl-3-{2-[4-(4-diphenylmethyl)piperazin-1-yl]ethyl}aminomethyl-1-phenylpyrazole;
3-{2-[4-(4-diphenylmethyl)piperazin-1-yl]ethyl}aminomethyl-5-(2-furyl)-1-phenylpyrazole;
1,5-diphenyl-3-{2-[4-(4-diphenylmethyl)piperazin-1-yl]ethyl}aminomethylpyrazole;
1-t-butyl-3-{2-[4-(4-diphenylmethyl)piperazin-1-yl]ethyl}aminomethyl-5-(4-methylphenyl)pyrazole;
1-t-butyl-5-(4-chlorophenyl)-3-{2-[4-(4-diphenylmethyl)piperazin-1-yl]ethyl}aminomethylpyrazole;
5-(4-cyclohexylphenyl)-3-{2-[4-(4-diphenylmethyl)piperazin-1-yl]ethyl}aminomethyl-1-phenylpyrazole;
3-{2-[4-(4-diphenylmethyl)piperazin-1-yl]ethyl}aminomethyl-1-phenyl-5-(4-piperidin-1-yl)phenylpyrazole;
3-{2-[4-(4-chlorobenzhydryl)piperazin-1-yl]ethyl}aminomethyl-5-methyl-1-phenylpyrazole;
1-t-butyl-3-{2-[4-(4-chlorobenzhydryl)piperazin-1-yl]ethyl}aminomethyl-5-propylpyrazole;
3-{2-[4-(4-chlorobenzhydryl)piperazin-1-yl]ethyl}aminomethyl-1-phenyl-5-propylpyrazole;
1-t-butyl-5-iso-butyl-3-{2-[4-(4-chlorobenzhydryl)piperazin-1-yl]ethyl}aminomethylpyrazole;
5-iso-butyl-3-{2-[4-(4-chlorobenzhydryl)piperazin-1-yl]ethyl}aminomethyl-1-phenylpyrazole;
3-{2-[4-(4-chlorobenzhydryl)piperazin-1-yl]ethyl}aminomethyl-5-(2-furyl)-1-phenylpyrazole;
3-{2-[4-(4-chlorobenzhydryl)piperazin-1-yl]ethyl}aminomethyl-1,5-diphenylpyrazole;
1-t-butyl-3-{2-[4-(4-chlorobenzhydryl)piperazin-1-yl]-ethyl}aminomethyl-5-(4-methylphenyl)pyrazole;
1-t-butyl-3-{2-[4-(4-chlorobenzhydryl)piperazin-1-yl]ethyl}aminomethyl-5-(4-chlorophenyl)pyrazole;
3-{2-[4-(4-chlorobenzhydryl)piperazin-1-yl]ethyl}aminomethyl-5-(4-cyclohexylphenyl)-1-phenylpyrazole;
3-{2-[4-(4-chlorobenzhydryl)piperazin-1-yl]ethyl}aminomethyl-1-phenyl-5-(4-piperidine-1-ylphenyl)pyrazole;
3-{2-[4-(2,3-dimethylphenyl)piperazin-1-yl]propyl}aminomethyl-5-methyl-1-phenylpyrazole;
3-{2-[4-(2,3-dimethylphenyl)piperazin-1-yl]propyl}aminomethyl-1,5-diphenylpyrazole;
3-{2-[4-(4-diphenylmethyl)piperazin-1-yl]propyl}aminomethyl-5-methyl-1-phenylpyrazole;
3-{2-[4-(4-diphenylmethyl)piperazin-1-yl]propyl}aminomethyl-1,5-diphenylpyrazole;
3-{2-[4-(2,3-dimethylphenyl)piperazin-1-yl]ethyl}methylaminomethyl-5-methyl-1-phenylpyrazole;
3-{2-[4-(2,3-dimethylphenyl)piperazin-1-yl]ethyl}methylaminomethyl-1-phenyl-5-propylpyrazole;
3-{2-[4-(2,3-dimethylphenyl)piperazin-1-yl]ethyl}ethylaminoethyl-5-methyl-1-phenylpyrazole;
3-{2-[4-(2,3-dimethylphenyl)piperazin-1-yl]ethyl}ethylaminoethyl-1-phenyl-5-propylpyrazole; and
3-{2-[4-(2,3-dimethylphenyl)piperazin-1-yl]propyl}ethylaminoethyl-1-phenyl-5-propylpyrazole.

3. A method of preparing a compound of Formula I or its pharmaceutically acceptable salt as defined in claim 1, comprising treating the compound of Formula II and the compound of Formula III with a reducing agent according to the following reaction scheme:

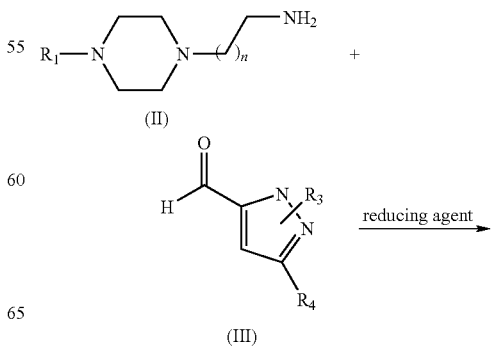

-continued

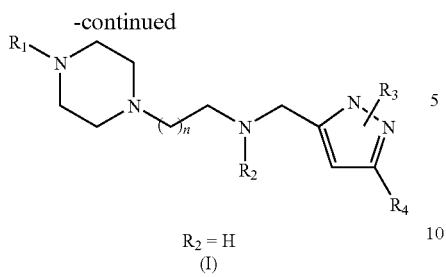

$R_2 = H$
(I)

wherein $R_1$ represents phenyl optionally substituted with from one to five of nitro, methyl, chloro, or methoxy; 1,1-diphenyl methyl wherein the phenyl groups are optionally substituted with one to five of chloro or methyl; or phenyl substituted with 2-fluoro;

$R_2$ is hydrogen;

$R_3$ represents methyl, propyl, isobutyl, cyclohexyl, phenyl optionally substituted with one or more of methyl, chloro, or methoxy; naphthyl, or piperidinyl;

$R_4$ represents hydrogen, $C_{1-6}$ alkyl, 2-furyl, or phenyl optionally substituted with one to five of chloro, methyl, methoxy, cyclohexyl, or piperidinyl groups; and n represents an integer from 0 to 3.

4. A method of preparing the compound of Formula I as defined in claim 1 wherein $R_2$ is methyl or ethyl, comprising reacting a compound having the formula

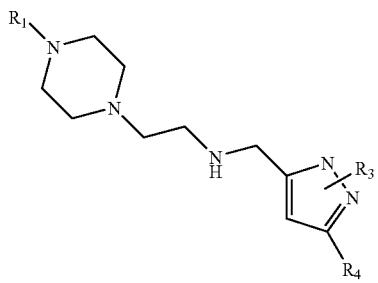

with an aldehyde of Formula $R_2$CHO in the presence of a reducing agent, wherein $R_1$ represents phenyl optionally substituted with from one to five of nitro, methyl, chloro, or methoxy; 1,1-diphenyl methyl wherein the phenyl groups are optionally substituted with one to five of chloro or methyl; or phenyl substituted with 2-fluoro;

$R_2$ is methyl or ethyl;

$R_3$ represents methyl, propyl, isobutyl, cyclohexyl, phenyl optionally substituted with one or more of methyl, chloro, or methoxy; naphthyl, or piperidinyl;

$R_4$ represents hydrogen, $C_{1-6}$ alkyl, 2-furyl, or phenyl optionally substituted with from one to five of chloro, methyl, methoxy, cyclohexyl, or piperidinyl; and n is an integer from 0 to 3.

5. The method of claim 3 or claim 4, wherein the reducing agent is selected from the group consisting of $NaBH_4$, $NaBH(OAc)_3$, $NaBH_2(OAc)_2$, $NaBH_3OAc$, $NaBH_3CN$, $KBH_4$ and $KBH(OAc)_3$.

6. A composition comprising a piperazinylalkylpyrazole compound of claim 1 as an active ingredient.

7. A method for treating epilepsy, pain or high blood pressure, comprising administering a therapeutically effective amount of the composition of claim 6 to a patient in need thereof.

8. A method for treating epilepsy, pain or high blood pressure comprising administering a therapeutically effective amount of the compound of claim 1 or its pharmaceutically acceptable salts to an animal in need thereof.

9. The method of claim 8 wherein the animal is a human being.

* * * * *